US010416106B1

(12) United States Patent
Pruessner

(10) Patent No.: US 10,416,106 B1
(45) Date of Patent: Sep. 17, 2019

(54) REMOTE WIRELESS MOISTURE SENSORS FOR IRRIGATION

(71) Applicant: Sprinkl.IO LLC, Richardson, TX (US)

(72) Inventor: Daniel Morgan Pruessner, Richardson, TX (US)

(73) Assignee: Sprinkl.IO LLC, Richardson, TX (US)

( * ) Notice: Subject to any disclaimer, the term of this patent is extended or adjusted under 35 U.S.C. 154(b) by 0 days.

(21) Appl. No.: 15/910,545

(22) Filed: Mar. 2, 2018

(51) Int. Cl.
*G01N 27/22* (2006.01)
*G01N 33/24* (2006.01)
*G01N 27/04* (2006.01)
*A01G 25/16* (2006.01)

(52) U.S. Cl.
CPC ......... *G01N 27/223* (2013.01); *G01N 27/048* (2013.01); *G01N 33/246* (2013.01); *A01G 25/167* (2013.01)

(58) Field of Classification Search
CPC .................................................. A01G 25/167
See application file for complete search history.

(56) References Cited

U.S. PATENT DOCUMENTS

| | | | |
|---|---|---|---|
| 4,389,900 | A | 6/1983 | Gutierrez |
| 4,545,396 | A | 10/1985 | Miller et al. |
| 4,657,039 | A | 4/1987 | Bireley et al. |
| 4,683,904 | A | 8/1987 | Iltis |
| 4,909,070 | A | 3/1990 | Smith |
| 4,929,885 | A | 5/1990 | Dishman |
| 5,424,649 | A | 6/1995 | Gluck et al. |
| 7,170,302 | B2 | 1/2007 | Lee |
| 7,313,946 | B2 | 1/2008 | Matsuo |
| 8,089,287 | B2 | 1/2012 | Izadnegahdar |

(Continued)

FOREIGN PATENT DOCUMENTS

| | | |
|---|---|---|
| KR | 1020060006704 A | 1/2006 |
| KR | 1020120050881 A | 5/2012 |

OTHER PUBLICATIONS rayshobby.net, "Reverse Engineer a Cheap Wireless Moisture Sensor," Jul. 23, 2014, 8 pages, https://rayshobby.net/wordpress/reverse-engineer-a-cheap-wireless-soil-moisture-sensor/ (accessed on Dec. 18, 2017).

(Continued)

*Primary Examiner* — Jermele M Hollington
*Assistant Examiner* — Alvaro E Fortich
(74) *Attorney, Agent, or Firm* — Patterson Intellectual Property Law, P.C.; Gary L. Montle; Jerry Turner Sewell

(57) ABSTRACT

A remote wireless moisture sensing unit is insertable into soil. The sensing unit includes at least three capacitive sensors positioned at three spaced apart levels with respect to the surface of the soil. The capacitance of each sensor increases in the presence of increased moisture content of the soil proximate to the sensor. An analog multiplexer selectively routes each sensor to an input to a capacitively-controlled oscillator to cause the oscillator to generate a clock signal having a frequency responsive to the capacitance of the currently connected sensor and thus responsive to the moisture content proximate to the currently selected sensor. A processor generates a respective data value for the frequency corresponding to each sensor and transmits the data values for the sensors via a radio frequency transceiver. The data values are processed to determine the moisture content of the soil at the three sensor levels.

10 Claims, 18 Drawing Sheets

(56) References Cited

U.S. PATENT DOCUMENTS

| | | | |
|---|---|---|---|
| 9,804,113 | B2 | 10/2017 | Kumaran et al. |
| 2002/0000813 | A1* | 1/2002 | Hirono ............... G01R 27/2605 |
| | | | 324/690 |
| 2006/0261822 | A1 | 11/2006 | Fraser |
| 2009/0302870 | A1 | 12/2009 | Paterson et al. |
| 2010/0277185 | A1* | 11/2010 | Hughes ............... G01N 27/223 |
| | | | 324/664 |
| 2013/0214803 | A1 | 8/2013 | McFarlane et al. |
| 2016/0033437 | A1 | 2/2016 | Anjum et al. |
| 2016/0307430 | A1* | 10/2016 | Chen ....................... G08B 6/00 |

OTHER PUBLICATIONS

"Capacitive Soil Moisture Sensor SKU:SEN0193," DFROBOT, Shanghai, China, May 25, 2017, 6 pages, https://www.dfrobot.com/product-1385.html (accessed on Dec. 18, 2017).

Shukla, Sanjay and Holt, Nathan, "Using Multi-Sensor Soil Moisture Probes to Decide When and How Long to Run Drip Irrigation," University of Florida IFAS Extension, AE505, Jul. 2014, pp. 1-6, (as archived on Dec. 29, 2015, at https://web.archive.org/web/20151229172231/http://edis.ifas.ufl.edu/pdffiles/AE/AE50500.pdf).

Hanson, Blaine R. and Peters, Douglas, "Soil type affects accuracy of dielectric moisture sensors," California Agriculture, May-Jun. 2000, pp. 43-47.

Lee, Hun Gil, Authorized Officer, Korean Intellectual Property Office, International Application Division, International Search Report and Written Opinion of the International Searching Authority, Jun. 14, 2019, 14 pages.

* cited by examiner

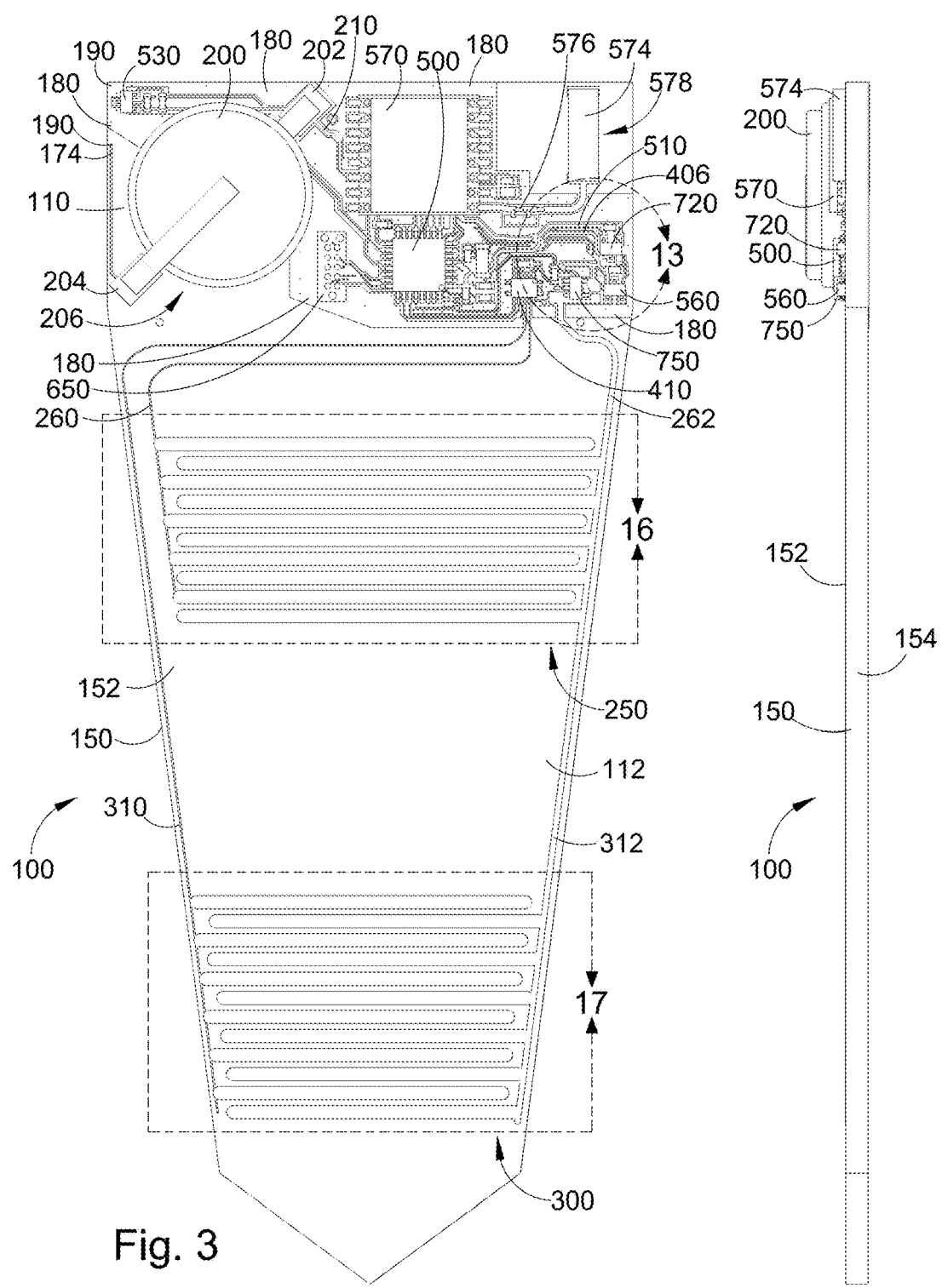
Fig. 3
Fig. 4
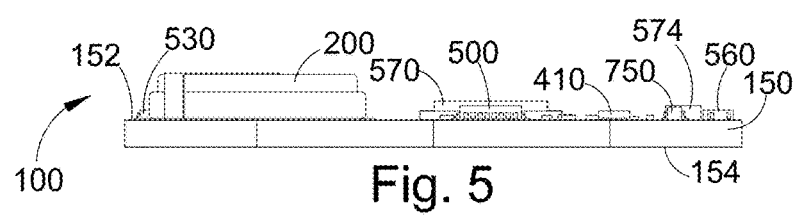
Fig. 5

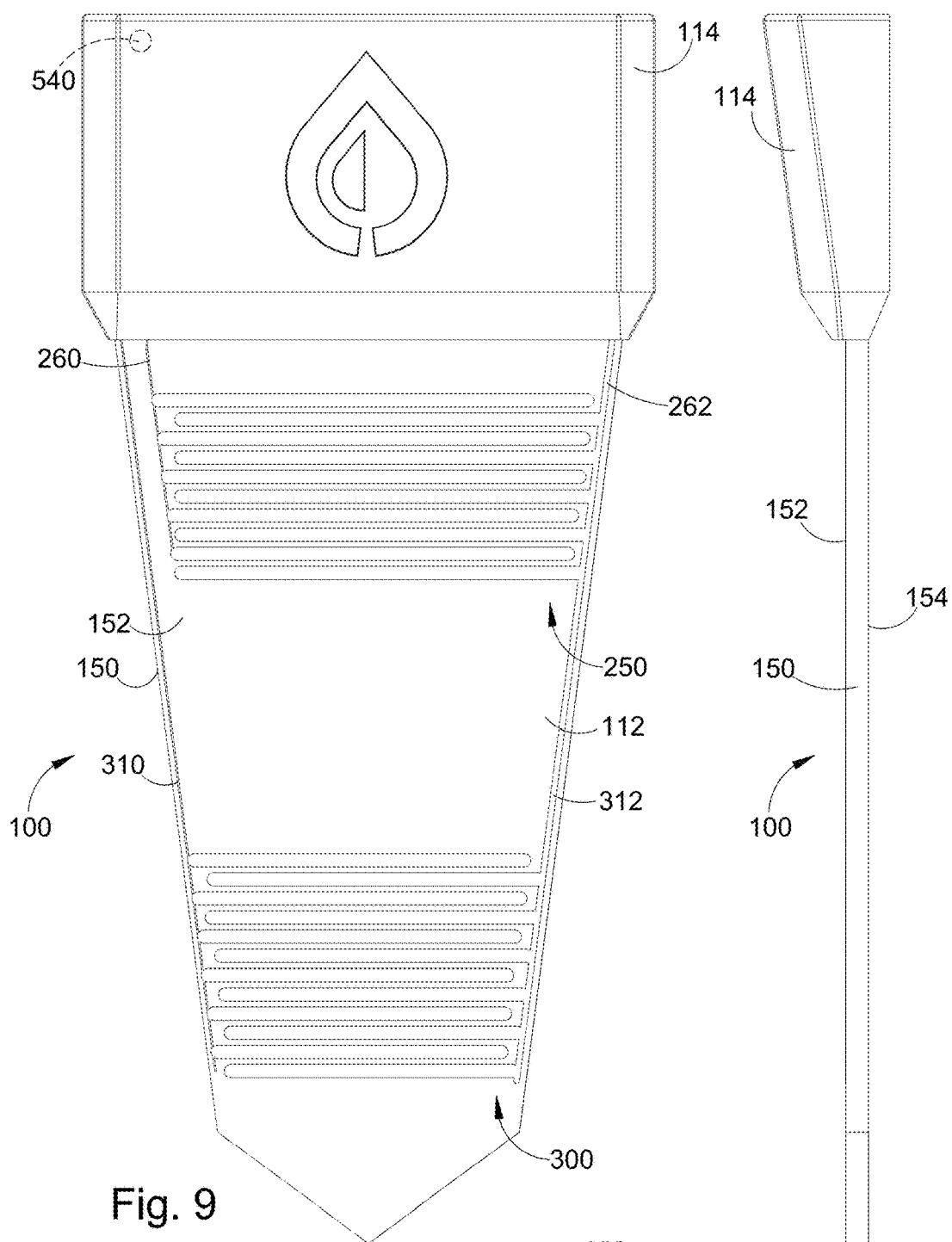
Fig. 9
Fig. 10
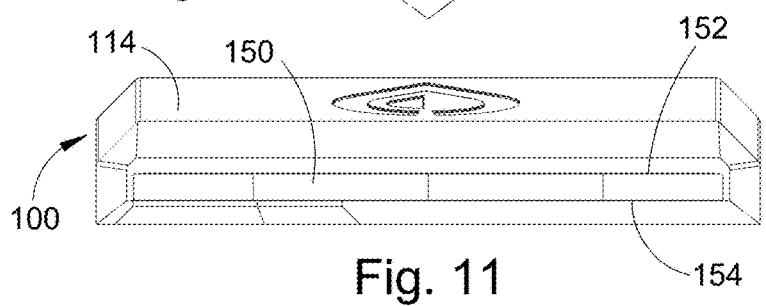
Fig. 11

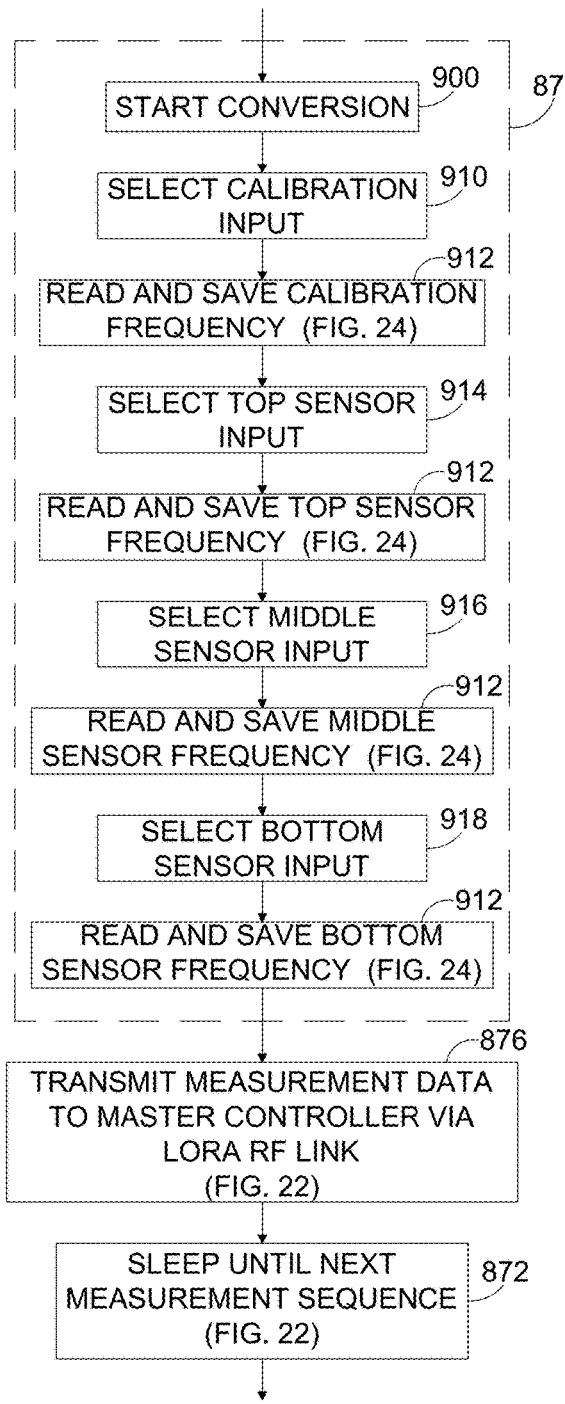
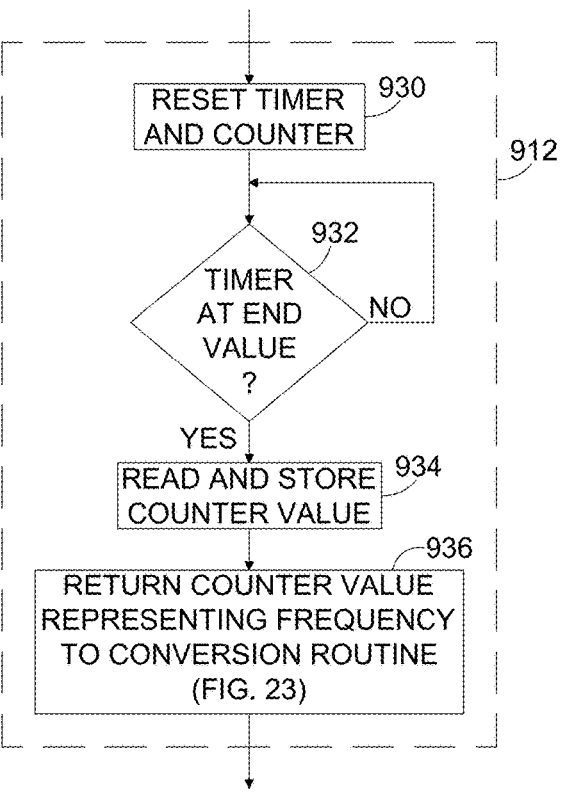
Fig. 23
Fig. 24

REMOTE WIRELESS MOISTURE SENSORS FOR IRRIGATION

RELATED APPLICATIONS

Field of the Invention

The present invention is in the field of irrigation control systems, and, more particularly, is in the field of moisture sensors that provide soil condition information to irrigation controllers.

BACKGROUND OF THE INVENTION

Programmable irrigation controllers are well-known and are available in a number of different configurations. Historically, programmable irrigation controllers included motor-driven timers that selectively turned on irrigation valves at selected times of the day, on selected days of the week and for selected time durations. The irrigation controllers included a power source at a selected voltage (e.g., 24 volts AC in some systems). The voltage from the power source was first routed to a first selected valve to enable water to flow to sprinklers in a first irrigation area for a first time duration. The voltage from the power source was then routed to a second selected valve to enable water to flow to sprinklers in a second irrigation area for a second time duration. Further valves were subsequently enabled to water additional irrigation areas. The irrigation sequence may have been repeated on a daily basis, may have occurred on certain days of the week, or may have skipped certain days. Setting up the original motor-driven timers was time-consuming and could be challenging for many users.

Over the years, the irrigation controllers with motor-driven timers have been replaced with fully electronic systems with liquid crystal displays (LCDs) and with much greater flexibility in programming the irrigation schedules for multiple irrigation areas. For example, some irrigation areas can be programmed to water on a daily basis, other irrigation areas can be programmed to water on certain days of the week, and other irrigation areas can be programmed to water multiple times in a single day. Regardless of the flexibility of the more recent programmable controllers, many controllers will adhere to the programmed irrigation schedule even while the irrigation areas are being irrigated naturally during a rainfall. It is not unusual to drive by a grassy area during a heavy rainfall and see the sprinklers operating at the same time.

Many conventional sprinkler systems have rain sensor input terminals that can be electrically connected to a rain sensor that collects and accumulates rain. When a sufficient amount of water is accumulated in the sensor, the sensor opens a circuit between the input terminals that causes the programmable controller to discontinue the programmed irrigation schedule until the accumulated rainfall has dissipated (e.g., by evaporation). Such rain sensors may be adequate for many irrigation systems such as, for example, irrigation systems for lawns or other areas where the soil conditions are uniform, the amount of shade is consistent, and the crop (e.g., lawn grass, food crops, or the like) are the same (e.g., require similar amounts of water to thrive). However, many irrigation systems provide water to non-uniform locations. For example, one area may comprise an unshaded lawn, another area may comprise a number of trees, and another area may comprise flower beds. The types of soil in the areas may be different such that one area has a soil that retains moisture and another area needs frequent replenishment of water. Thus, a simple rain sensor may not be adequate to provide sufficient information to an irrigation controller to determine when to provide water to multiple areas with different requirements.

Although remote moisture sensors are available, known remote moisture sensor suffer from deficiencies that reduce the efficacy of such sensors. For example, many known sensors have at least a portion of the sensor located above the surface of the soil being sensed. Thus, such sensors must be protected from damage. Other sensors required solar power to maintain the sensors in an operable state for an extended duration. Other sensors have a limited capability of determining the moisture content of the soil because the sensors only sensed moisture at a single depth or the sensors sense over a broad range of depths without identifying the differing moisture contents at different depths.

SUMMARY OF THE INVENTION

In view of the foregoing, a need exists for an improved remote moisture sensor that can be buried entirely below the surface, can sense moisture content at two or more discrete depths, can wirelessly transmit the moisture information to a base station, and can operate for a substantial time using a single battery.

One aspect of the embodiments disclosed herein is a remote wireless moisture sensing unit that is insertable into soil. The sensing unit includes at least three capacitive sensors positioned at three spaced apart levels with respect to the surface of the soil. The capacitance of each sensor increases in the presence of increased moisture content of the soil proximate to the sensor. An analog multiplexer selectively routes each sensor to an input to a capacitively-controlled oscillator to cause the oscillator to generate a clock signal having a frequency responsive to the capacitance of the currently connected sensor and thus responsive to the moisture content proximate to the currently selected sensor. A processor generates a respective data value for the frequency corresponding to each sensor and transmits the data values for the sensors via a radio frequency transceiver. The data values are processed to determine the moisture content of the soil at the three sensor levels.

Another aspect of the embodiments disclosed herein is a moisture sensor that is insertable into soil. The moisture sensor comprises a printed circuit board having an upper end and a lower end and having a front surface and a rear surface. A first capacitive sensor is positioned on one of the front surface and the back surface of the printed circuit board and is positioned in a first selected location with respect to the upper end of the printed circuit board. The first capacitive sensor has a first capacitance responsive to moisture content of soil proximate to the first capacitive sensor. A second capacitive sensor is positioned on one of the front surface and the back surface of the printed circuit board and is positioned in a second selected location with respect to the upper end of the printed circuit board. The second selected location is farther from the upper end than the first selected location. The second capacitive sensor has a second capacitance responsive to moisture content of soil proximate to the second capacitive sensor. A third capacitive sensor is positioned on one of the front surface and the back surface of the printed circuit board and is positioned in a third selected location with respect to the upper end of the printed circuit board. The third selected location is farther from the upper end than the second selected location. The third capacitive sensor has a third capacitance responsive to moisture content of soil proximate to the third capacitive sensor. A processing and transmission subsystem is positioned on at least one of the front surface and the back surface of the printed circuit board proximate to the upper end of the printed circuit board. The processing and transmission subsystem is coupled to each of the first, second and third capacitive sensors. The processing and transmission subsystem generates a first data value responsive to the first capacitance, generates a second data value responsive to the second capacitance and generates a third data value responsive to the third capacitance. The processing and transmission subsystem transmits the first, second and third data values via a radio frequency output signal.

In certain embodiments in accordance with this aspect, the processing and transmission subsystem includes a capacitor having a fixed fourth capacitance substantially unaffected by the moisture content of the soil proximate to the moisture sensor. The processing and transmission subsystem generates a calibration data value responsive to fourth fixed fourth capacitance and transmits the calibration data value along with the first, second and third data values.

In certain embodiments in accordance with this aspect, the processing and transmission subsystem includes a temperature sensor that generates an electrical output signal responsive to the temperature of soil proximate to the temperature sensor. The processing and transmission subsystem generates a temperature sensor data value and transmits the temperature sensor data value along with the first, second and third data values.

In certain embodiments in accordance with this aspect, the processing and transmission subsystem includes an analog multiplexer having at least a first analog input connected to the first capacitive sensor, a second analog input connected to the second capacitive sensor and a third analog input connected to the third capacitive sensor. The analog multiplexer has an analog output. The analog multiplexer is controlled to selectively connect the first capacitive sensor to the analog output for a first time duration, to selectively connect the second capacitive sensor to the analog output for a second time duration and to selectively connect the third capacitive sensor to the analog output for a third time duration. A capacitance-controlled oscillator has an input coupled to the analog output of the capacitor and has an output that generates clock signal. The oscillator is responsive to the first capacitive sensor connected to the analog output to generate the clock signal at a first frequency during the first time duration. The oscillator is responsive to the second capacitive sensor connected to the analog output to generate the clock signal at a second frequency during the second time duration. The oscillator is responsive to the third capacitive sensor connected to the analog output to generate the clock signal at a third frequency during the third time duration. A processor receives the clock signal from the oscillator. The processor determines the first frequency to generate the first data value, determines the second frequency to generate the second data value and determines the third frequency to generate the third data value.

In certain embodiments in accordance with this aspect, the processing and transmission subsystem includes a calibration capacitor having a fixed fourth capacitance substantially unaffected by the moisture content of the soil proximate to the moisture sensor. The analog multiplexer is controlled to selectively connect the calibration capacitor to the analog output for a fourth time duration. The oscillator is responsive to the calibration capacitor connected to the analog output to generate the clock signal at a fourth frequency during the fourth time duration. The processor determines the fourth frequency to generate a calibration data value. The processing and transmission subsystem transmits the calibration data value in the radio frequency output signal along with the first, second and third data values.

Another aspect of the embodiments disclosed herein is a method for determining moisture content of soil at three spaced apart levels below the surface of the soil. The method comprises inserting a moisture sensing unit into the soil with a first capacitive sensor at a first level below the soil surface, with a second capacitive sensor at a second level below the soil surface, and with a third capacitive sensor at a third level below the soil surface. The second level is farther below the soil surface than the first level. The third level is farther below the soil surface than the second level. The method further comprises selecting the first capacitive sensor as an input to a capacitively controlled clock generator during a first time duration. The clock generator generates an output clock signal at a first frequency during the first time duration. The first frequency is responsive to a capacitance of the first capacitive sensor. The capacitance of the first capacitive sensor is responsive to the moisture content of soil proximate to the first capacitive sensor at the first level. The method further comprises selecting the second capacitive sensor as an input to a capacitively controlled clock generator during a second time duration. The clock generator generates an output clock signal at a second frequency during the second time duration. The second frequency is responsive to a capacitance of the second capacitive sensor. The capacitance of the second capacitive sensor is responsive to the moisture content of soil proximate to the second capacitive sensor at the second level. The method further comprises selecting the third capacitive sensor as an input to a capacitively controlled clock generator during a third time duration. The clock generator generates an output clock signal at a third frequency during the third time duration. The third frequency is responsive to a capacitance of the third capacitive sensor. The capacitance of the third capacitive sensor is responsive to the moisture content of soil proximate to the third capacitive sensor at the third level. The method further comprises determining the first frequency and generating a first data value responsive to the first frequency; determining the second frequency and generating a second data value responsive to the second frequency; determining the third frequency and generating a third data value responsive to the third frequency. The method further comprises transmitting the first, second and third data values via a radio frequency signal as representations of the moisture content of the soil at the first, second and third levels, respectively.

In certain embodiments in accordance with this aspect, the method further comprises selecting a calibration capacitor as an input to the clock generation during a fourth time duration. The clock generator generates the output clock signal at a fourth frequency. The fourth frequency is responsive to a capacitance of the calibration capacitor. The method determines the fourth frequency and generates a calibration data value responsive to the fourth frequency. The method transmits the calibration data value along with the first, second and third data values via the radio frequency signal.

In certain embodiments in accordance with this aspect, the method further comprises generating an electrical output signal responsive to the temperature of soil proximate to the temperature sensor; generating a temperature sensor data value responsive to the electrical output signal; and transmitting the temperature sensor data value along with the first, second and third data values via the radio frequency signal.

In certain embodiments in accordance with this aspect, the first capacitive sensor, the second capacitive sensor and the third capacitive sensor are selected via an analog multiplexer that couples a selected one of the capacitive sensors to an analog output of the analog multiplexer. The analog output of the analog output of the analog multiplexer is coupled to an input of the clock generator. The clock generator generates the clock signal at a frequency responsive to the capacitance of the respective capacitive sensor selected by the analog multiplexer. The frequency of the clock signal from the clock generator is determined for each selected capacitive sensor to produce a respective data value responsive to the frequency for each selected capacitive sensor and thereby responsive to the respective capacitance of each selected capacitive sensor. The capacitance increases with increased moisture content, and the frequency decreases with increased moisture content.

In certain embodiments in accordance with this aspect, the analog multiplexer selects a calibration capacitor during a fourth time duration. The calibration capacitor has a fixed capacitance substantially unaffected by the moisture content of the soil proximate to the moisture sensor. The clock generator is responsive to the calibration capacitor connected to the analog output to generate the clock signal at a fourth frequency during the fourth time duration. The fourth frequency of the clock signal is determined to produce a fourth data value responsive to the fourth frequency and thereby responsive to the capacitance of the calibration capacitor. The fourth data value is transmitted with the first, second and third data values to provide a reference value for comparison with the first, second and third data values

BRIEF DESCRIPTIONS OF THE DRAWINGS

The foregoing aspects and other aspects of the disclosure are described in detail below in connection with the accompanying drawings in which:

FIG. 3 illustrates a front elevational view of the view of the moisture sensing unit of FIG. 1;

FIG. 4 illustrates a right side elevational view of the view of the moisture sensing unit of FIG. 1;

FIG. 5 illustrates a bottom plan view of the view of the moisture sensing unit of FIG. 1;

FIG. 9 illustrates a front elevational view of the view of the moisture sensing unit and protective upper cover of FIG. 7;

FIG. 10 illustrates a right side elevational view of the view of the moisture sensing unit and protective upper cover of FIG. 7;

FIG. 11 illustrates a bottom plan view of the view of the moisture sensing unit and protective upper cover of FIG. 7;

FIG. 23 illustrates a flowchart of the steps within the step of measuring moisture, temperature and battery voltage of the flowchart of FIG. 22;

FIG. 24 illustrates a flowchart of the subroutine to read and store the counter value representing frequency.

DESCRIPTION OF ILLUSTRATED EMBODIMENTS

Figure 1:
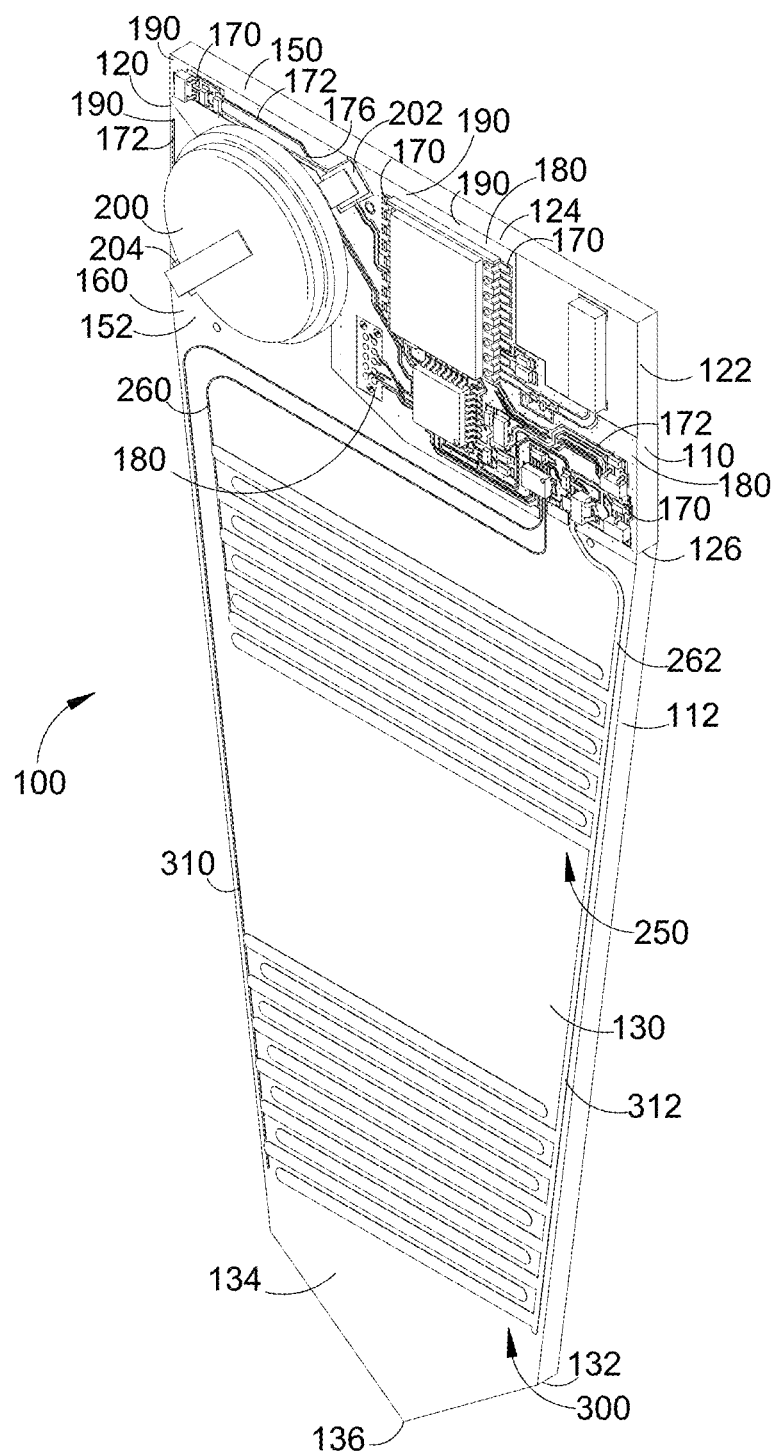
FIG. 1 illustrates a front perspective view of a wireless moisture sensing unit shown without a protective upper cover.

As used throughout this specification, the words "front," "rear," "top," "bottom," "upper," "lower," "longitudinal," "upward," "downward," "proximal," "distal," and other similar directional words are used with respect to the views being described. It should be understood that the remote wireless moisture sensor described herein can be used in various orientations and is not limited to use in the orientations illustrated in the drawing figures.

FIGS. 1-12 illustrate a remote moisture sensing unit 100 in accordance with embodiments of the present invention. FIGS. 1-6 illustrate the moisture sensing unit prior to installation of a protective upper cover. The moisture sensing unit comprises a generally rectangular upper body portion 110 (see FIGS. 7-12) and a stake-shaped (tapered) lower body portion 112. FIGS. 7-12 illustrate moisture sensing unit of FIGS. 1-6 wherein the upper body portion is covered, at least in part, with a protective cover 114. At least a portion of the lower body portion does not include a protective cover and remains exposed as discussed below.

As shown in FIGS. 1-6, the upper body portion 110 has a width from a first side 120 to a second side 122 (FIG. 3) of approximately 70 millimeters and has a length (height) of approximately 30 millimeters from an uppermost end 124 to a first transition location 126 with the tapered lower body portion. An uppermost portion 130 of the lower body portion tapers gradually from a greater width (e.g., approximately 70 millimeters) at the first transition location to a lesser width (e.g., approximately 39.9 millimeters) at a second transition location 132 approximately 115.2 millimeters from the first transition location. A lowermost portion 134 of the lower body portion tapers from the second transition location to an angular lowermost end 136. For example, in the illustrated embodiment, the lowermost portion has a height of approximately 14.7 millimeters from the second transition location to the lowermost end. In the illustrated embodiment, the lowermost end forms an angle of approximately 107 degrees. The lengths and the angle are not critical and are provided by way of examples only.

Figure 2:
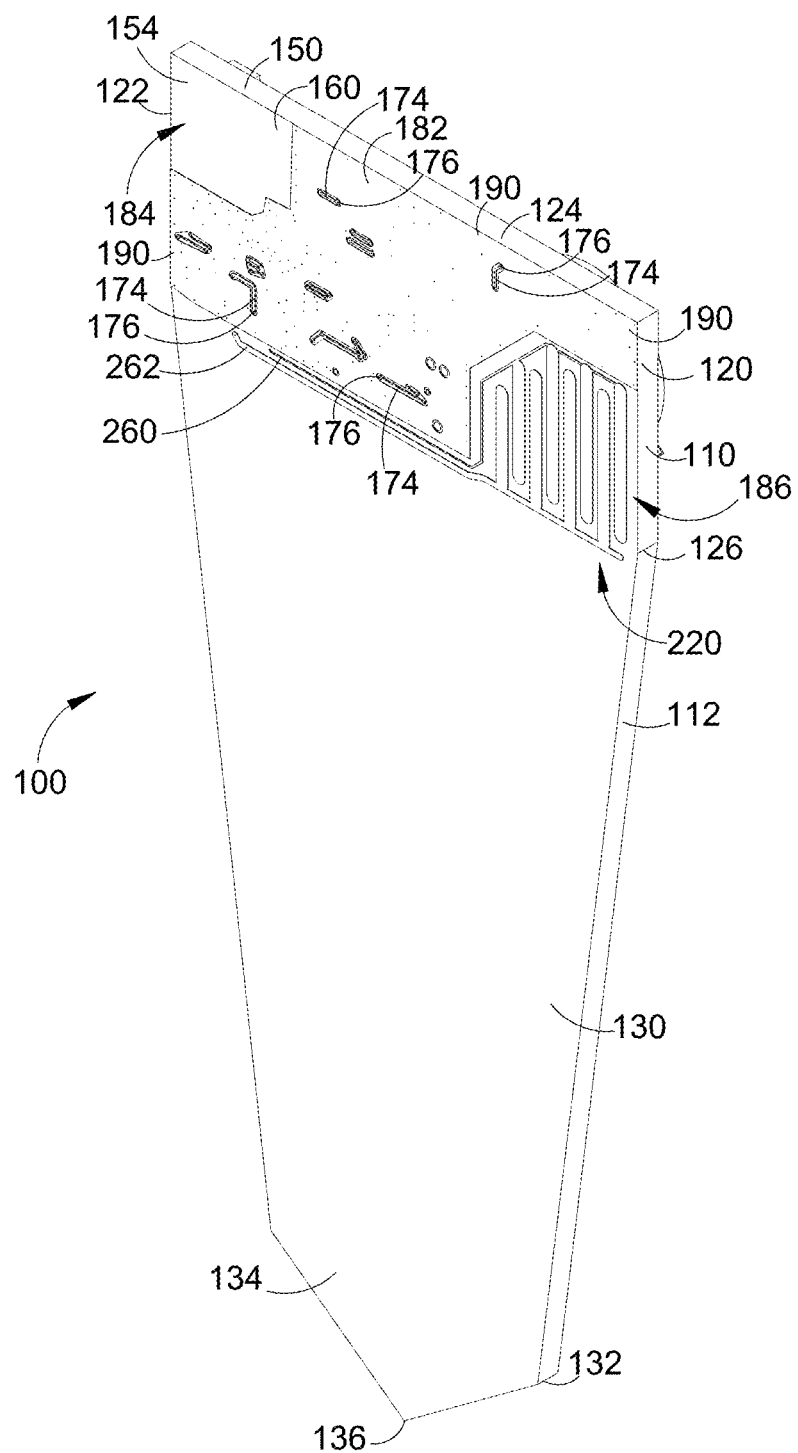
FIG. 2 illustrates a rear perspective view of the moisture sensing unit of FIG. 1.
Figure 6:
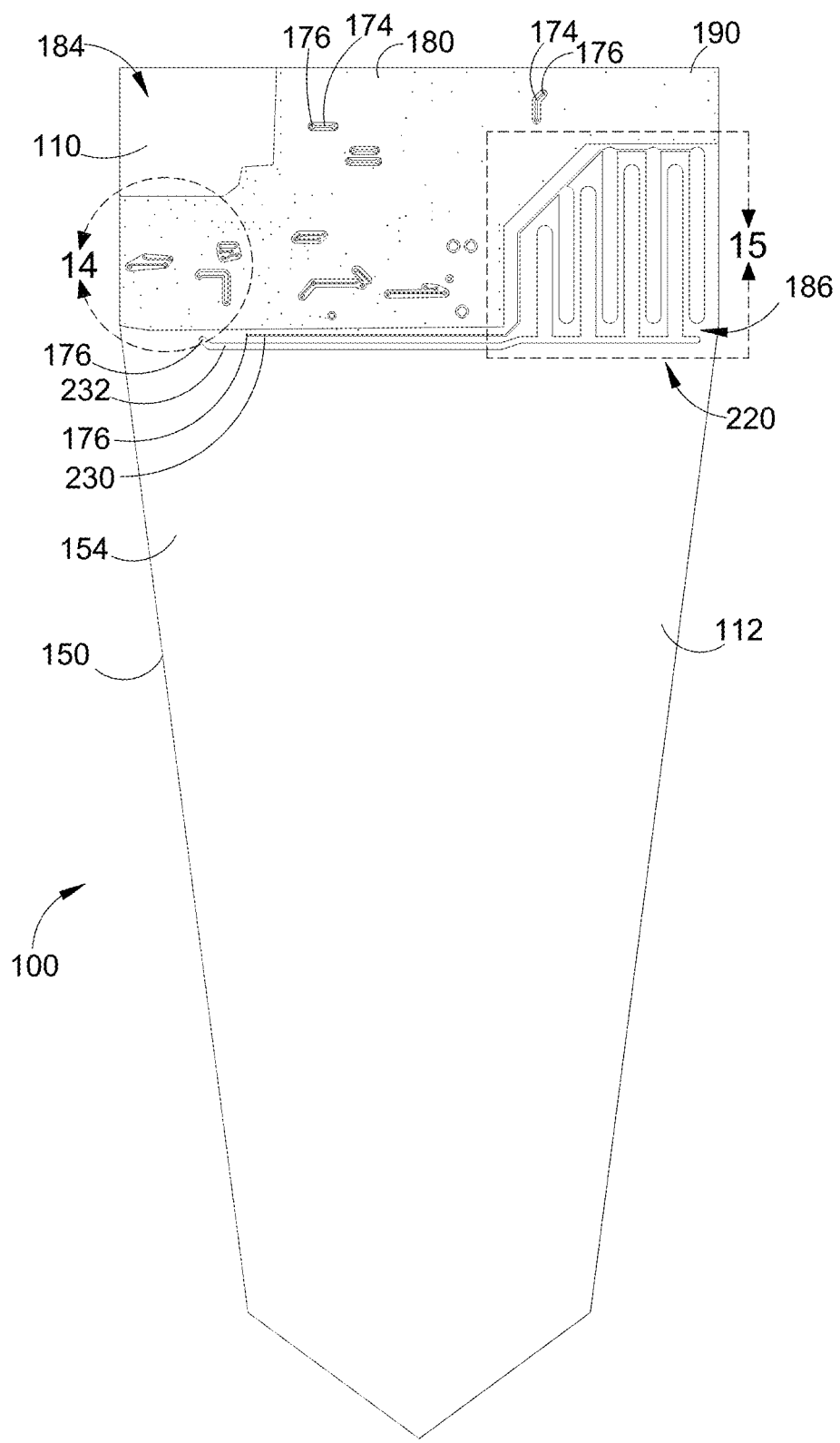
FIG. 6 illustrates a rear elevational view of the view of the moisture sensing unit of FIG. 1.
Figure 7:
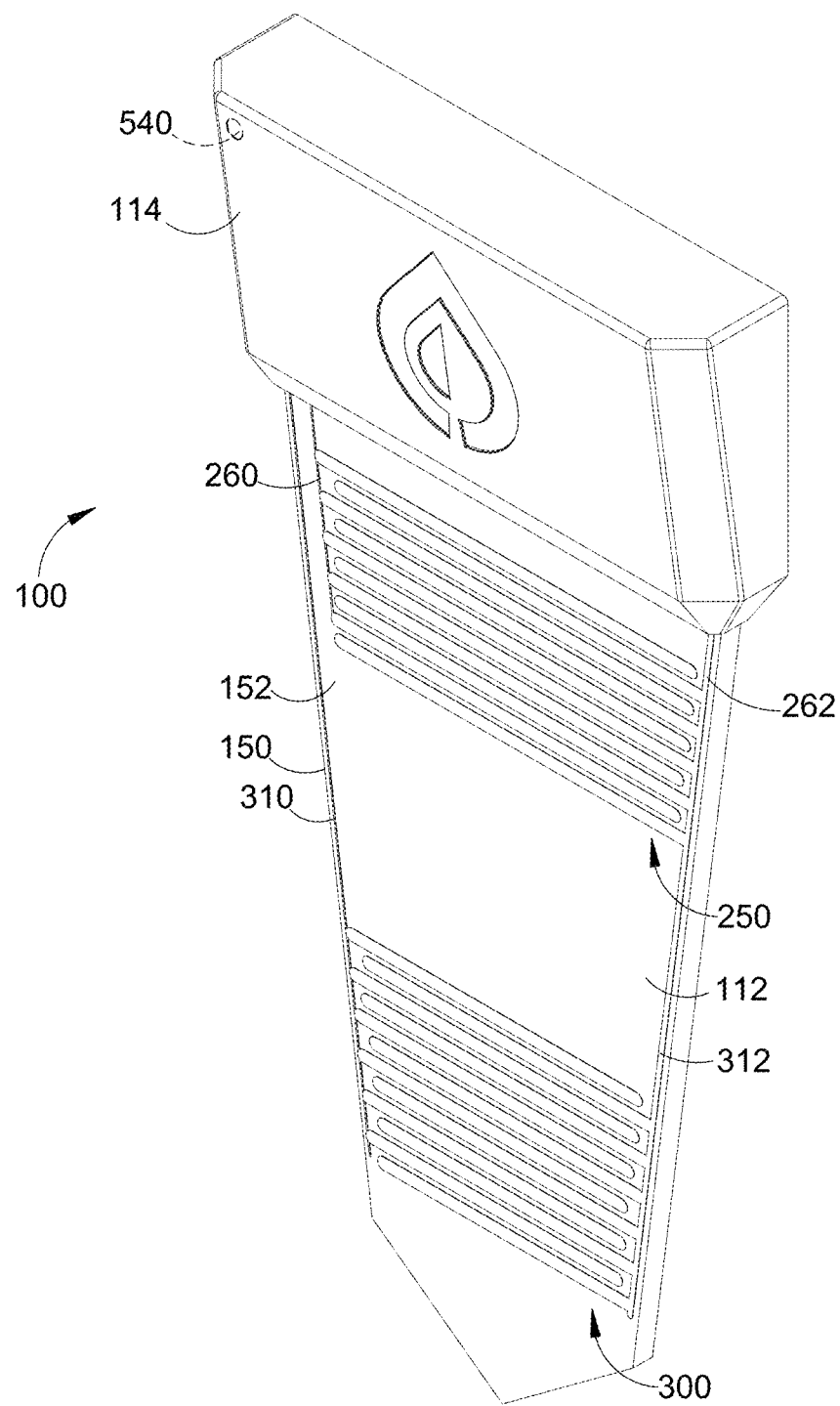
FIG. 7 illustrates a front perspective view of the moisture sensing unit of FIG. 1 with a protective upper cover installed.
Figure 8:
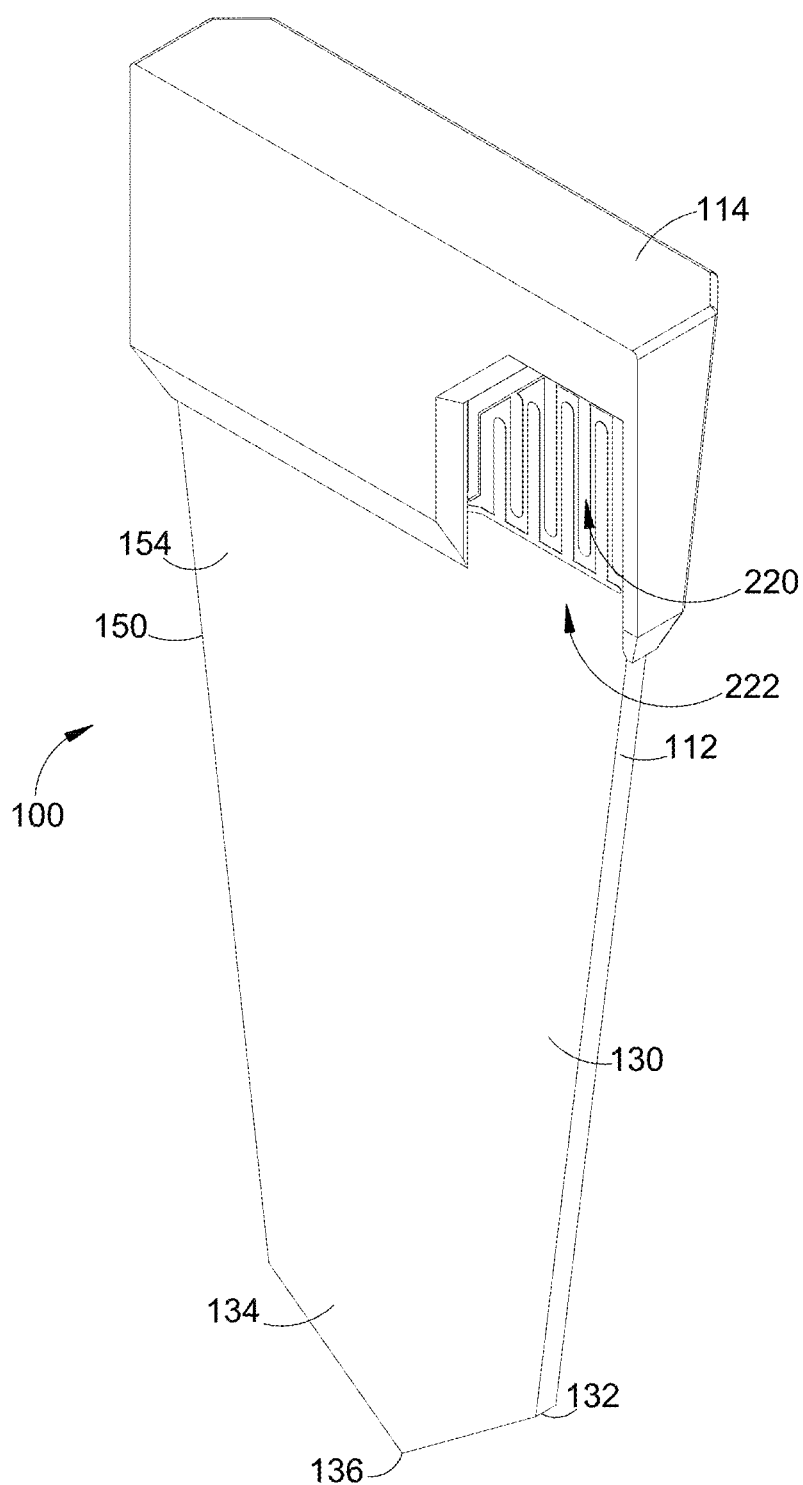
FIG. 8 illustrates a rear perspective view of the moisture sensing unit and protective upper cover of FIG. 7.

In the illustrated embodiment, the upper body portion 110 and the lower body portion 112 of the moisture sensing unit comprise a single printed circuit board (PCB) 150 (FIGS. 8 and 9) having circuit features formed on a front (first) surface 152 (FIGS. 1 and 3) and a rear (second) surface 154 (FIGS. 2 and 6).

In certain embodiments, the PCB 150 comprises a substrate 160 of conventional fiber-reinforced plastic (FRP) glass epoxy or another suitable insulating material. For example, one such material is FRP-4 glass epoxy, which is commercially available from a number of sources. In the illustrated embodiment, the PCB is a two-sided printed circuit board, which initially has a suitable electrically conductive material fixed to the front surface 152 and the rear surface 154 of the insulating material. For example, the electrically conductive material may be copper. Selected portions of the copper are removed from the two surfaces of the insulating material (e.g., by conventional etching techniques or other suitable copper removal techniques) to form mounting pads 170 on the front surface on the front surface of the upper body portion. Front conductive traces 172 are formed on the front surface and rear conductive traces 174 are formed on the rear surface. The PCB may also include a plurality of electrically conductive circuit interconnect vias (also referred to as feedthroughs) 176 between certain conductive traces and mounting pads on the front surface and certain conductive traces on the rear surfaces to complete electrical interconnections that cannot be completed on the front surface without using jumper wires or long conductive traces.

The front surface 152 of the upper body portion 110 further includes a plurality of front ground plane portions 180. The front ground plane portions occupy areas between the front conductive traces 172 and the mounting pads with bare buffer areas separating the group plane portions from the traces and pad. The rear surface 154 of the upper body portion further includes a rear ground plane 182, which occupies a substantial portion of the area of the rear surface except for a first rear ungrounded area 184 and a second rear ungrounded area 186, which are discussed below, and except for buffer areas surrounding the rear conductive traces 174. The front and rear ground plane portions are interconnected by a plurality of electrically conductive ground vias 190 that cause the ground plane portions to be electrically interconnected.

As discussed above, the upper body portion 110 has the mounting pads 170 and the front conductive traces 172 on the front surface 152 and has the rear conductive traces 174 on the rear surface 154 of the PCB 150. The upper body portion also has substantial areas occupied by the rear ground plane 182 and the front ground plane portions 180. In contrast, the lower body portion 112 of the PCB only has conductive traces (described below) on the front surface.

As shown in FIG. 3, for example, a portion of the front surface 152 of the upper body portion 110 to the left of the centerline is occupied by a battery 200, such as, for example, a CR2450 coin cell battery, which produces 3 volts between a positive terminal and a negative terminal. The battery is soldered to a positive solder pad 202 and to a negative solder pad 204. The negative solder pad is coupled to the rear ground plane 182 by one of the front conductive traces 172 and at least one of the ground vias 190. The positive solder pad is coupled to a plurality of the conductive traces forming a VCC bus 210 A substantial portion of the front surface beneath the battery forms a first front ungrounded area 206, which is juxtaposed with the second rear ungrounded area 186.

Figure 12:
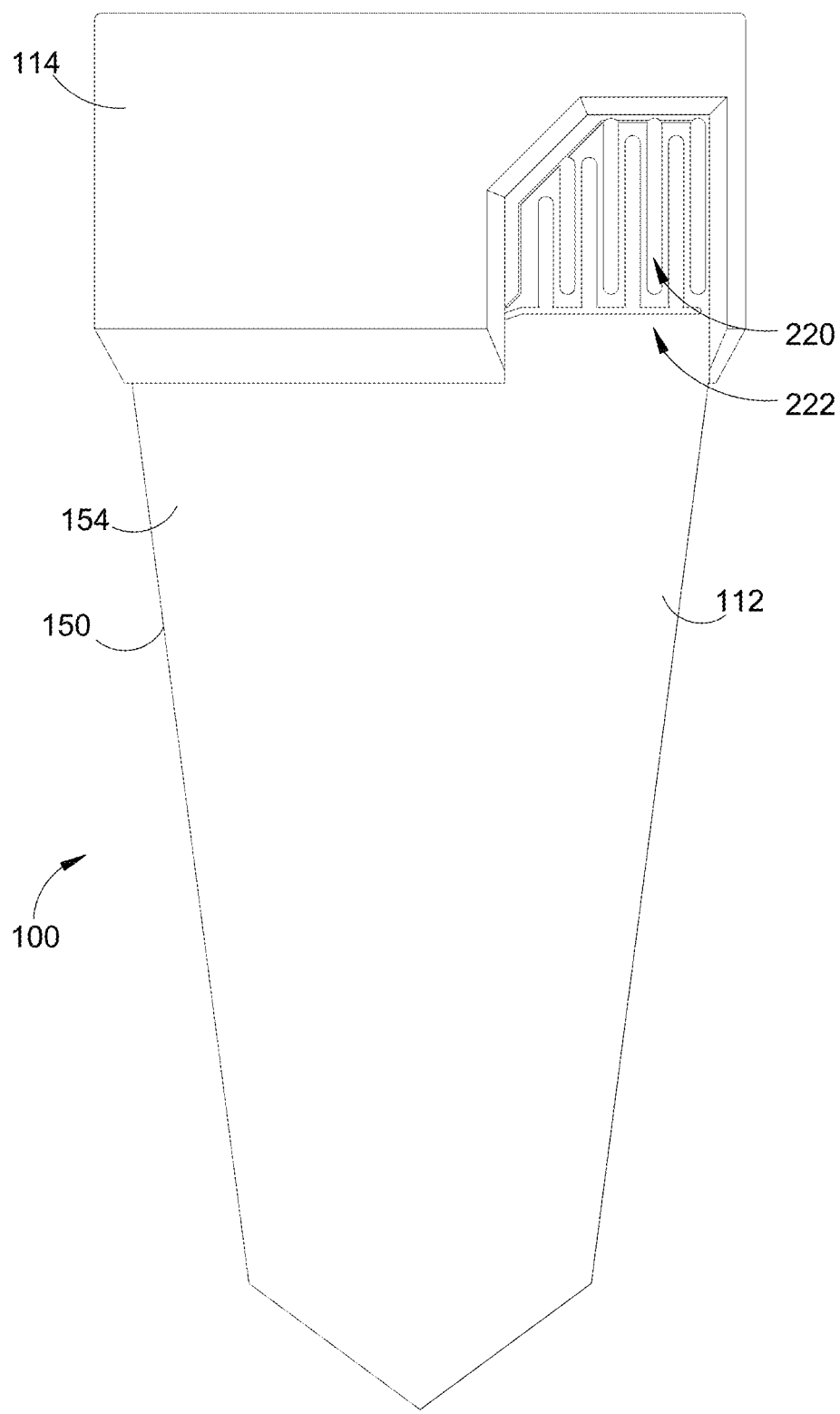
FIG. 12 illustrates a rear elevational view of the view of the moisture sensing unit and protective upper cover of FIG. 7.

As shown in FIGS. 2, 6, 8, 12 and 15, a portion of the second (rear) surface 154 of the upper body portion 110 in the second rear ungrounded area 186 is etched to form a first sensing capacitor 220. The first sensing capacitor is juxtaposed with the battery 200 on the first surface. As shown in FIGS. 9 and 12, the first sensing capacitor is exposed through an opening 222 in the upper protective cover 114. The edges of the opening are sealed by a suitable sealing material (not shown) to inhibit moisture and other contaminants from reaching the other circuitry protected by the upper protective cover.

Figure 15:
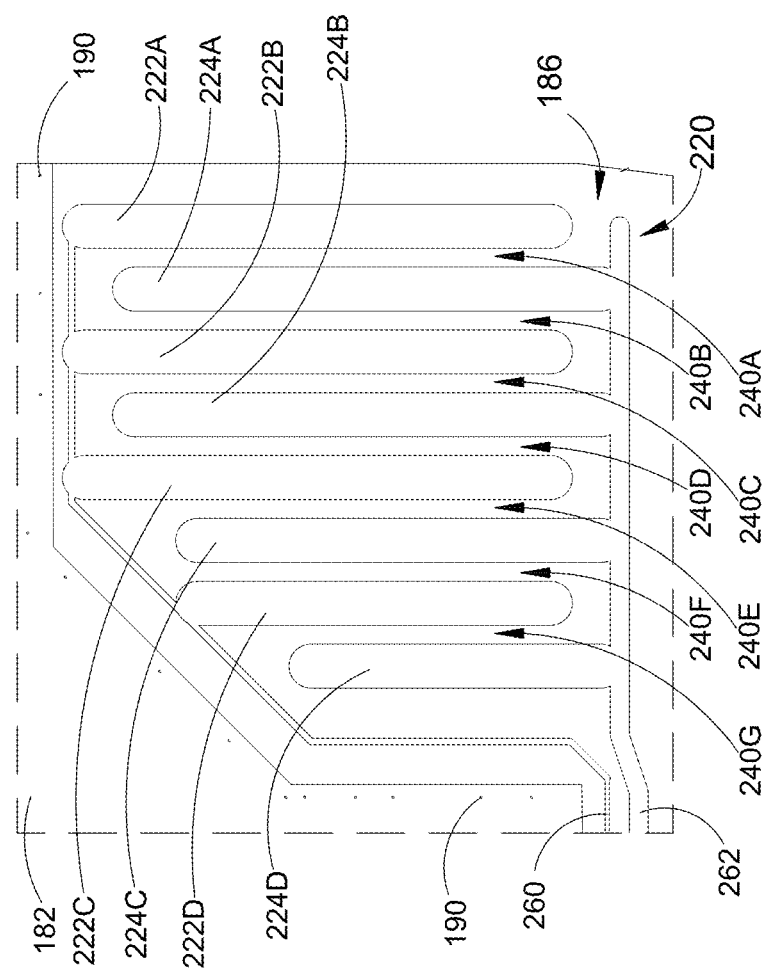
FIG. 15 illustrates an enlarged rear elevational view of the upper portion of the moisture sensing unit within an area—15—of FIG. 6 showing the conductive traces forming the first (upper) sensor capacitor in more detail.
Figure 16:
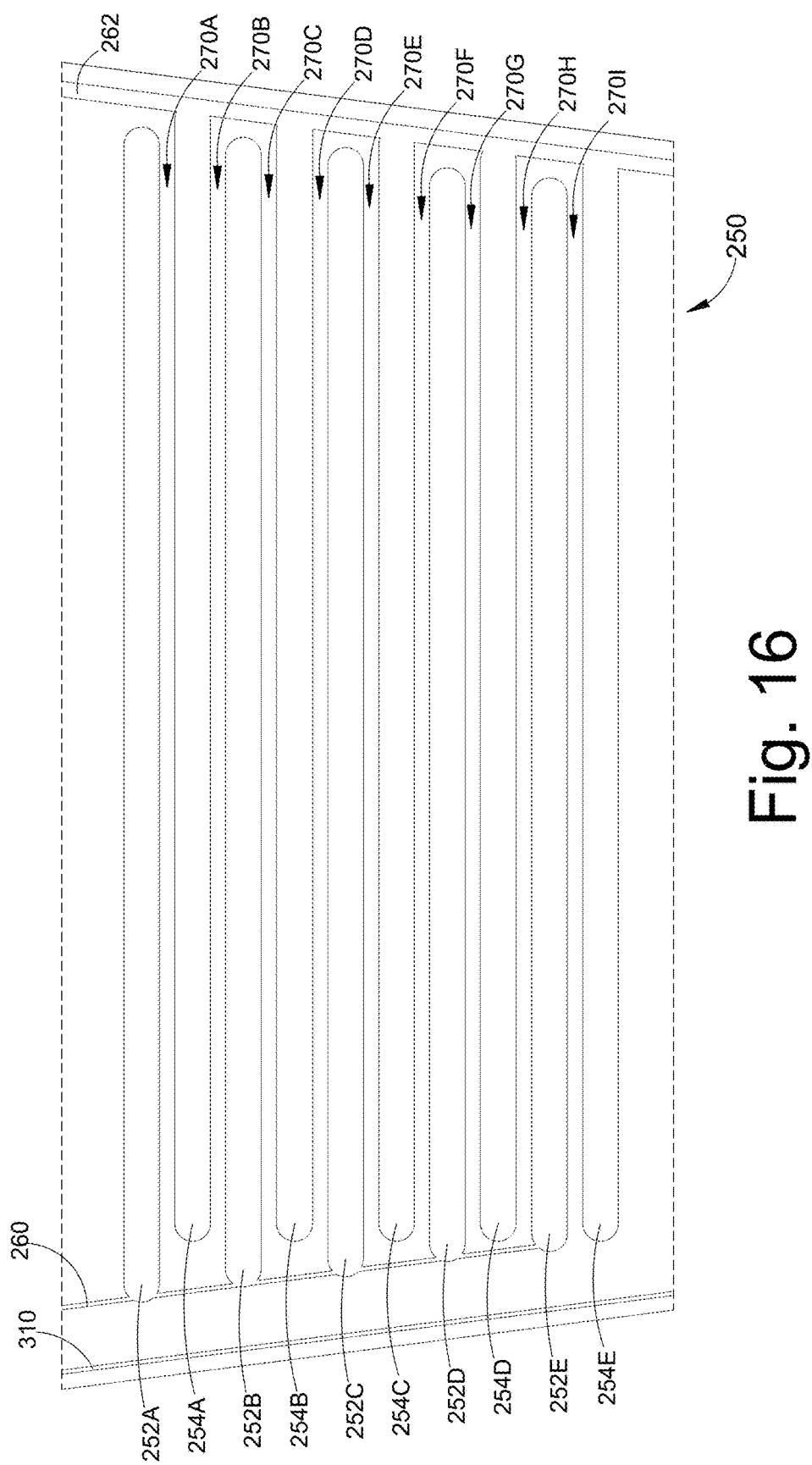
FIG. 16 illustrates an enlarged front elevational view of the lower portion of the moisture sensing unit within an area—16—of FIG. 3 showing the conductive traces forming the second (middle) sensor capacitor in more detail.

As shown in FIG. 15, the first sensing capacitor 220 comprises an array of interleaved conductive elements comprising a plurality of respective signal elements 222A-D and a plurality of respective ground elements 224A-D. In the illustrated embodiment, four signal elements and four ground elements are provided. More or fewer elements may be provided. Also, the number of signal elements may differ from the number of ground elements in other embodiments. The signal and ground elements are mutually parallel with each other. The four signal elements are electrically interconnected with each other and are connected to a first sensing capacitor signal line 230. The four ground elements are electrically connected to each other and are connected to a first sensing capacitor ground line 232.

In the illustrated embodiment, the first signal element 222A of the first sensing capacitor 220 is spaced apart from the first ground element 224A to form a first capacitive element 240A. The second signal element 222B is spaced apart from the first ground element 224A to form a second capacitive element 240B. The second signal element 222B is also spaced apart from the second ground element 224B to form a third capacitive element 240C. The third signal element 222C is spaced apart from the second ground element 224B to form a fourth capacitive element 240D. The third signal element 222C is also spaced apart from the third ground element 224C to form a fifth capacitive element 240E. The fourth signal element 222D is spaced apart from the third ground element 224C to form a sixth capacitive element 240F. The fourth signal element 222D is also spaced apart from the fourth ground element 224D to form a seventh capacitive element 240G. In the illustrated embodiment, each of the signal and ground elements has a width of approximately 0.07 inch (approximately 1.78 millimeters) and has a perpendicular thickness with respect to the surface of the PCB 150 of approximately 0.035 millimeters. The signal and ground elements are spaced apart by gaps of approximately 0.03 inch (approximately 0.76 millimeter).

The parallel lengths forming the seven capacitors vary from approximately 16.75 millimeters for each of the first through fourth capacitive elements, to approximately 14.21 millimeters for each of the fifth and sixth capacitive elements to approximately 9.64 millimeters for the seventh capacitive element. Each capacitive element includes a relatively small parallel plate capacitance between the 0.035-millimeter edges of adjacent signal and ground elements and a relatively large coplanar capacitance between the 1.78-millimeter wide traces through the PCB material. The seven capacitive elements are electrically connected in parallel, which results in a total nominal capacitance of approximately 9 nanofarads. As discussed below in the description of the electronic circuitry, the first sensing capacitor signal line 230 is provided to the electronic circuitry as a first sensing signal input. The first sensing capacitor ground line 232 is connected to the circuit ground in a manner described below.

The nominal total capacitance of the first sensing capacitor 220 can be changed modifying one or more of the number of sensing element pairs, the spacing between sensing elements, the widths of the traces, and the distance of juxtaposition (e.g., the lengths) of the sensing elements in each pair. The capacitance can also be changed by changing the thickness of the copper layer forming the sensing elements.

When the moisture sensing unit is inserted into soil with top of the protective cover 114 substantially even with the surface level of the soil, the first sensing capacitor is located in a first sensing range from approximately 12 millimeters to approximately 33 millimeters below the surface level of the soil.

Figure 17:
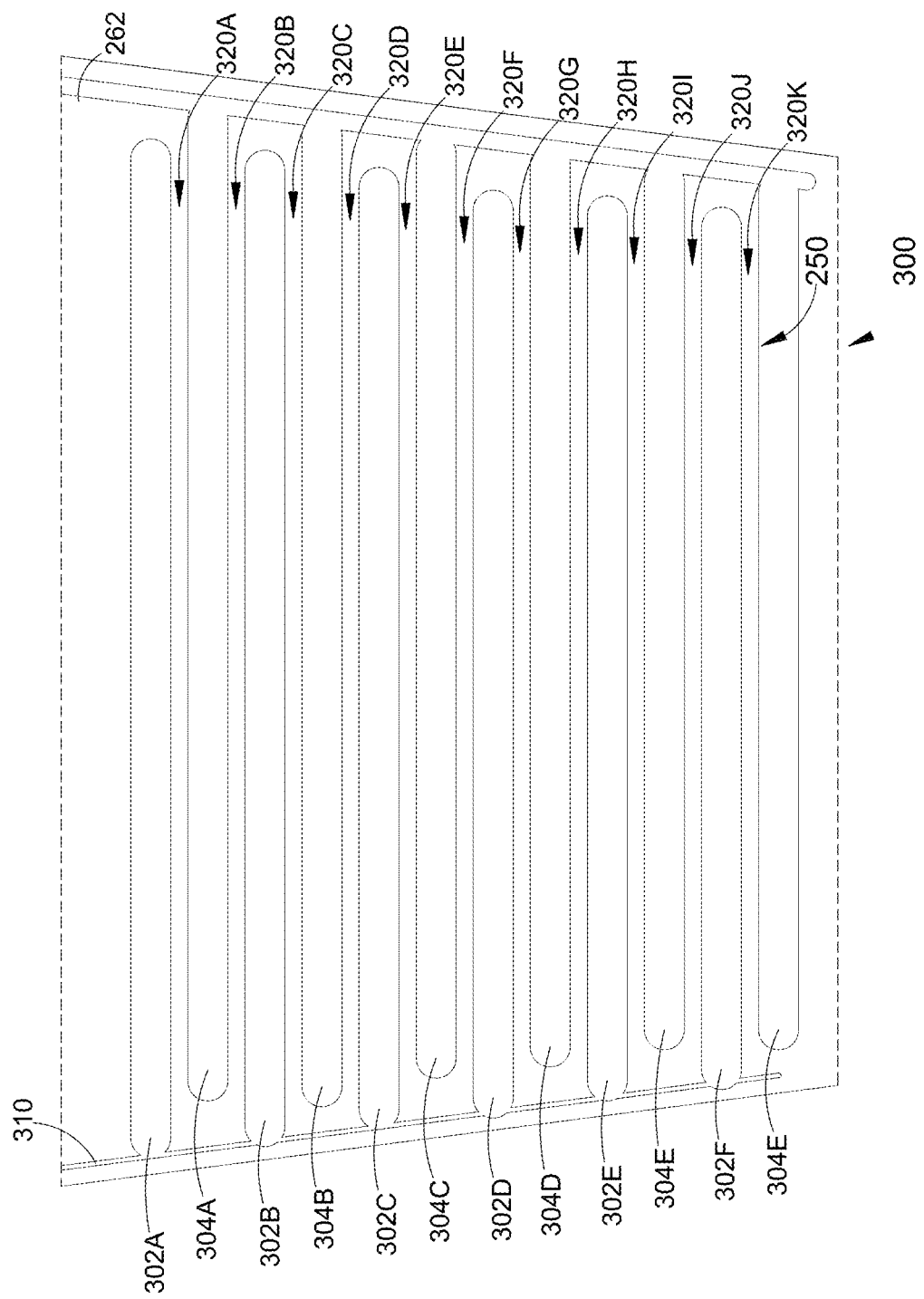
FIG. 17 illustrates an enlarged front elevational view of the lower portion of the moisture sensing unit within an area—17—of FIG. 3 showing the conductive traces forming the third (lower) sensor capacitor in more detail.

As shown in FIGS. 1, 3 and 17, a second sensing capacitor 250 is formed on the front surface 122 of the lower body portion 112 of the remote moisture sensing unit 100. The second sensing capacitor is located on an upper half of the lower body portion as shown.

The second sensing capacitor 250 comprises an array of interleaved conductive elements comprising a plurality of respective signal elements 252A-E and a plurality of respective ground elements 254A-E. In the illustrated embodiment, five signal elements and five ground elements are provided. More or fewer elements may be provided. Also, the number of signal elements may differ from the number of ground elements in other embodiments. The signal and ground elements are mutually parallel with each other. The five signal elements are electrically interconnected with each other and are connected to a second sensing capacitor signal line 260. The five ground elements are electrically connected to each other and are connected to a second sensing capacitor ground line 262.

In the illustrated embodiment, the first signal element 252A of the second sensing capacitor 250 is spaced apart from the first ground element 254A to form a first capacitive element 270A. The second signal element 252B is spaced apart from the first ground element 254A to form a second capacitive element 270B. The second signal element 252B is also spaced apart from the second ground element 254B to form a third capacitive element 270C. The third signal element 252C is spaced apart from the second ground element 254B to form a fourth capacitive element 270D. The third signal element 252C is also spaced apart from the third ground element 254C to form a fifth capacitive element 270E. The fourth signal element 252D is spaced apart from the third ground element 254C to form a sixth capacitive element 270F. The fourth signal element 252D is also spaced apart from the fourth ground element 254D to form a seventh capacitive element 270G. The fifth signal element 252E is spaced apart from the fourth ground element 254D to form an eighth capacitive element 270H. The fifth signal element 252E is also spaced apart from the fifth ground element 254E to form a ninth capacitive element 270I. In the illustrated embodiment, each of the signal and ground elements has a width of approximately 1.78 millimeters and has a thickness of approximately 0.035 millimeters. The signal and ground elements are spaced apart by gaps of approximately 0.76 millimeter. The parallel lengths forming the nine capacitors vary from approximately 53.72 millimeters for the first capacitive element, to approximately 53.21 millimeters for each of the second and third capacitive elements, to approximately 52.7 millimeters for each of the fourth and fifth capacitive elements, to approximately 51.69 millimeters for each of the sixth and seventh capacitive elements, to approximately 51.18 millimeters for each of the eighth and ninth capacitive elements. Each capacitive element has a parallel plate capacitance and a coplanar capacitance formed between the adjacent signal and ground elements. The nine capacitive elements are electrically connected in parallel, which results in a total nominal capacitance of approximately 42 nanofarads. As discussed below in the description of the electronic circuitry, the second sensing capacitor signal line 260 is provided to the electronic circuitry as a first sensing signal input. The second sensing capacitor ground line 262 is connected to the circuit ground in a manner described below.

The nominal total capacitance of the second sensing capacitor 250 can be changed modifying one or more of the number of sensing element pairs, the spacing between sensing elements, the widths of the traces, and the distance of juxtaposition (e.g., the lengths) of the sensing elements in each pair. The capacitance can also be changed by changing the thickness of the copper layer forming the sensing elements.

Figure 18:
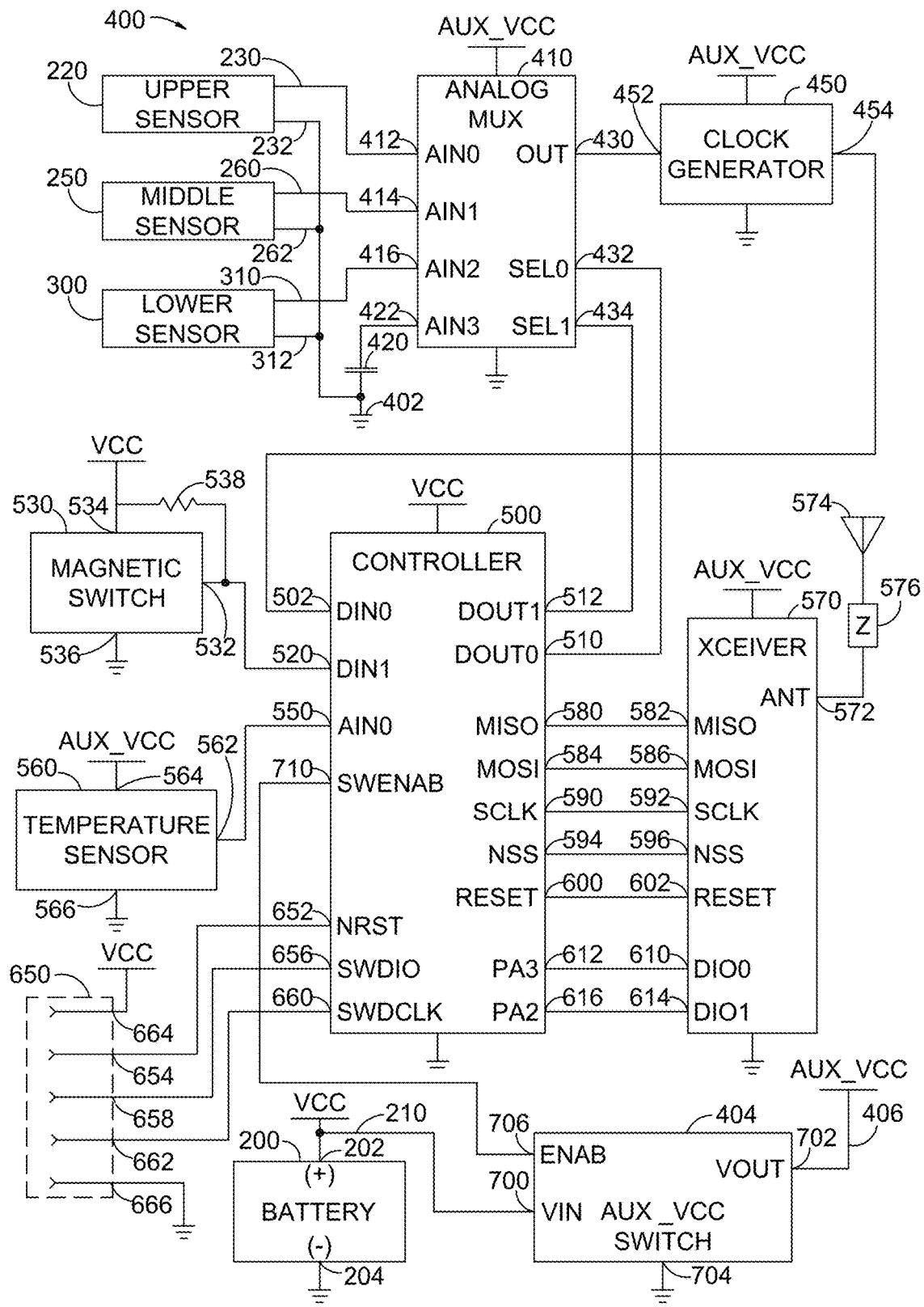
FIG. 18 illustrates a block diagram of the electronic circuitry mounted on the front and rear surfaces of the printed circuit board of FIGS. 1-17.

As shown in FIGS. 1, 3 and 18, a third sensing capacitor 300 is formed on the front surface 122 of the lower body portion 112 of the remote moisture sensing unit 100. The third sensing capacitor is located on a lower half of the lower body portion as shown.

The third sensing capacitor 300 comprises an array of interleaved conductive elements comprising a plurality of respective signal elements 302A-F and a plurality of respective ground elements 304A-F. In the illustrated embodiment, six signal elements and six ground elements are provided. More or fewer elements may be provided. Also, the number of signal elements may differ from the number of ground elements in other embodiments. The signal and ground elements are mutually parallel with each other. The six signal elements are electrically interconnected with each other and are connected to a third sensing capacitor signal line 310. The six ground elements are electrically connected to each other and are connected to a third sensing capacitor ground line 312, which, as illustrated in FIGS. 1 and 3, merges with the second sensing capacitor ground line 262.

In the illustrated embodiment, the first signal element 302A of the third sensing capacitor 300 is spaced apart from the first ground element 304A to form a first capacitive element 320A. The second signal element 230B is spaced apart from the first ground element 230A to form a second capacitive element 320B. The second signal element 302B is also spaced apart from the second ground element 304B to form a third capacitive element 320C. The third signal element 302C is spaced apart from the second ground element 304B to form a fourth capacitive element 320D. The third signal element 302C is also spaced apart from the third ground element 304C to form a fifth capacitive element 320E. The fourth signal element 302D is spaced apart from the third ground element 304C to form a sixth capacitive element 320F. The fourth signal element 302D is also spaced apart from the fourth ground element 304D to form a seventh capacitive element 320G. The fifth signal element 302E is spaced apart from the fourth ground element 304D to form an eighth capacitive element 320H. The fifth signal element 302E is also spaced apart from the fifth ground element 304E to form a ninth capacitive element 320I. The sixth signal element 302F is spaced apart from the fifth ground element 304E to form a tenth capacitive element 320J. The sixth signal element 302F is also spaced apart from the sixth ground element 304F to form an eleventh capacitive element 320K. In the illustrated embodiment, each of the signal and ground elements has a width of approximately 1.78 millimeters and has a thickness of approximately 0.035 millimeters. The signal and ground elements are spaced apart by gaps of approximately 0.76 millimeter. The parallel lengths forming the nine capacitors vary from approximately 41.05 millimeters for the first capacitive element, to approximately 40.54 millimeters for the second capacitive element, to approximately 40.79 millimeters for the third capacitive element, to approximately 40.03 millimeters for the fourth capacitive element, to approximately 38.77 millimeters for the fifth capacitive element, to approximately 37.75 millimeters for the sixth capacitive element, to approximately 37.25 millimeters for the seventh capacitive element, to approximately 36.99 millimeters for the eighth capacitive element, to approximately 36.23 millimeters for the ninth capacitive element, to approximately 35.73 millimeters for each of the tenth and eleventh capacitive elements. Each capacitive element has a parallel plate capacitance and a coplanar capacitance formed between the adjacent signal and ground elements. The eleven capacitive elements are electrically connected in parallel, which results in a total nominal capacitance of approximately 36 nanofarads. As discussed below in the description of the electronic circuitry, the third sensing capacitor signal line 310 is provided to the electronic circuitry as a third sensing signal input. The third sensing capacitor ground line 312 is connected to the circuit ground in a manner described below.

The nominal total capacitance of the third sensing capacitor 300 can be changed modifying one or more of the number of sensing element pairs, the spacing between sensing elements, the widths of the traces, and the distance of juxtaposition (e.g., the lengths) of the sensing elements in each pair. The capacitance can also be changed by changing the thickness of the copper layer forming the sensing elements.

As discussed above, the first sensing capacitor 220 is located in a first sensing range from approximately 12 millimeters to approximately 33 millimeters below the surface level of the soil when the moisture sensing unit 100 is inserted into soil with top of the protective cover 114 substantially even with the surface level of the soil. Under the same conditions, the second sensing capacitor 250 is located in a second sensing range from approximately 50 millimeters to approximately 75 millimeters below the surface level of the soil; and the third sensing capacitor 300 is located in a third sensing range from approximately 111 millimeters to approximately 141 millimeters below the surface level of the soil. Thus, the first, second and third sensing capacitors are centered at approximately 22.5 millimeters, 62.5 millimeters and 126 millimeters, respectively, below the surface of the soil to provide three distinct sensing regions.

Prior to installation of the upper protective cover, the entire PCB 150 is covered with a thin layer of a conventional negative photoresist material such as, for example, an epoxy-base polymer. When exposed to light (e.g., ultraviolet light), the photoresist material becomes insoluble and provides a permanent moisture-resistant barrier over the pads and traces on both the upper portion 112 and the lower portion 114. Thus, insertion of the moisture sensing unit 110 into moist soil does result in unwanted electrical connections between the elements of the three sensing capacitors 220, 250, 300. On the other hand, the moisture in the soil does affect the capacitance of the any sensing capacitor exposed to the moisture. For example, the material of the PCB 150 has a relative permittivity of approximately 4.7. In contrast, at 20° C., water has a relative permittivity of approximately 80. Thus, in water, the capacitance of an exposed sensing capacitors may increase by a factor of around 17 in comparison to the nominal capacitance of the sensing capacitor. Soil fully saturated with water may have a relative permittivity of 40-50, which may increase the capacitance by a factor of approximately 8.5 to 10.5 in comparison to the nominal capacitance.

FIG. 18 illustrates a block diagram of a sensing and communication system 400. The sensing and communication system is provided with power from the battery 200 via the VCC voltage bus 210 with respect to the front ground plane portions 180 and the rear ground plane 182. The rear ground plane and the front ground plane portions are electrically interconnected and are represented in FIG. 18 as single ground reference 402. The VCC voltage bus is connected directly to certain components of the sensing and communication system. Other components are provided with an auxiliary voltage AUX_VCC, which is selectively generated by an auxiliary voltage switch (AUX_VCC SWITCH) 404, which is described in more detail below. The auxiliary voltage is provided on an auxiliary voltage bus 406.

Figure 13:
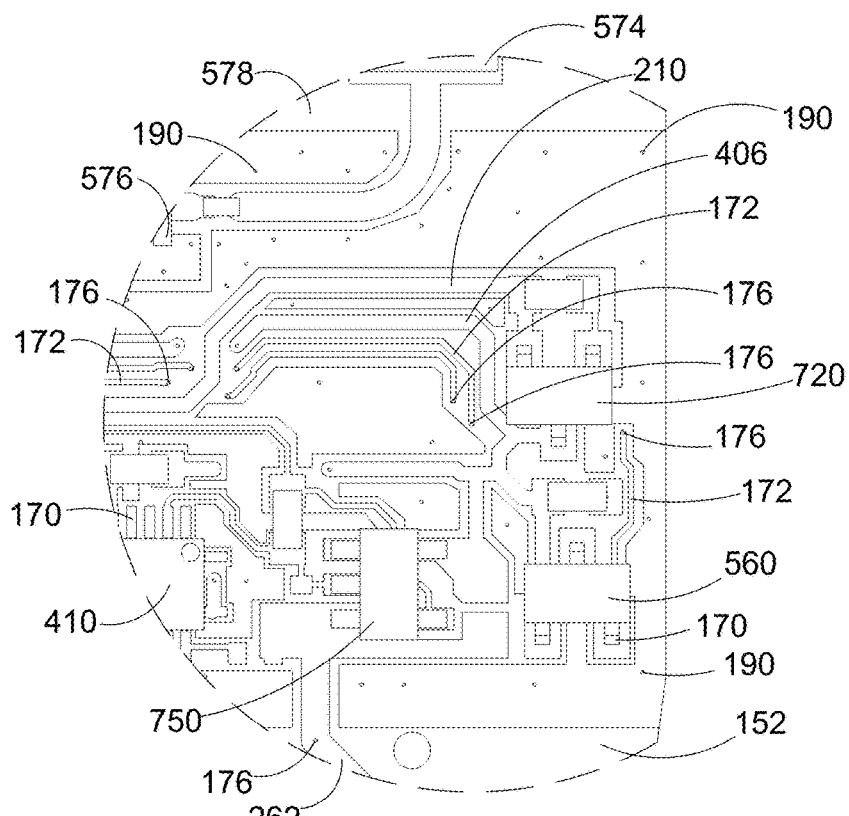
FIG. 13 illustrates an enlarged front elevational view of the upper portion of the moisture sensing unit within an area—13—of FIG. 3.
Figure 14:
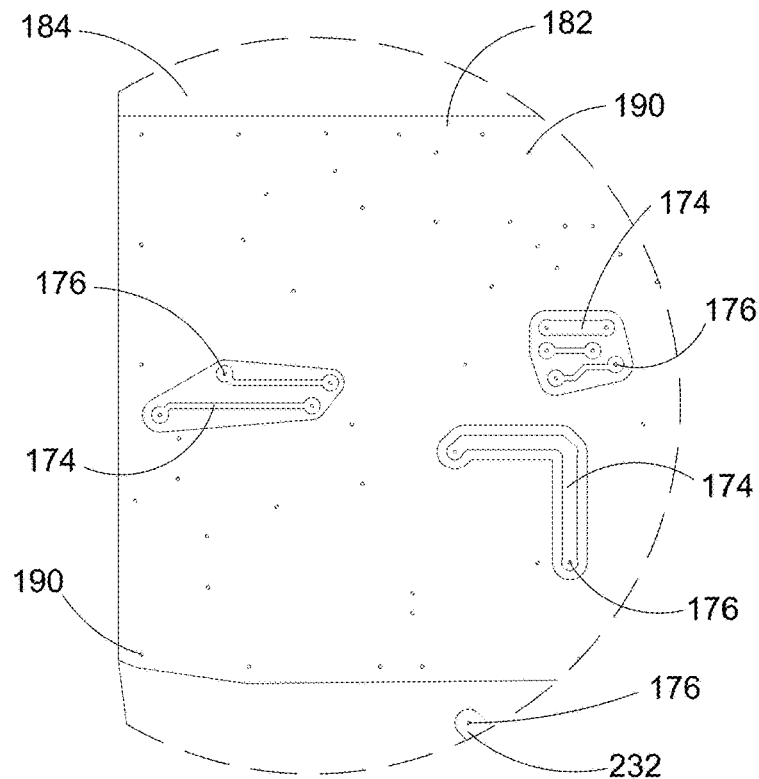
FIG. 14 illustrates an enlarged rear elevational view of the upper portion of the moisture sensing unit within an area—14—of FIG. 4, the rear elevational view in FIG. 14 aligned with the front elevational view of FIG. 13.

The first sensing capacitor signal line 230 and the first sensing capacitor ground line 232 connect the first sensing capacitor 220 to a sensing and communication system 400. The second sensing capacitor signal line 260 and the second sensing capacitor ground line 262 connect the second sensing capacitor 250 to the sensing and communication system. The third sensing capacitor signal line 310 and the third sensing capacitor ground line 312 connect the third sensing capacitor 300 to the sensing and communication system. As shown in FIGS. 13 and 14, the first sensing capacitor ground line is connected via a circuit interconnect via 176 to the second sensing capacitor ground line before the combined ground lines are connected to one of the front ground plane portions 180 on the front surface 152 of the printed circuit board 150 and are thus connected to the single ground reference 402 of the sensing and communication system.

The first sensing capacitor signal line 230 is connected as a first analog input signal to a first analog input (AIN0) terminal 412 of an analog multiplexer (ANALOG MUX) 410 in the sensing and communication system. The second sensing capacitor signal line 260 is connected as a second analog input signal to a second analog input (AIN1) terminal 414 of the analog multiplexer. The third sensing capacitor signal line 310 is connected as a third analog input signal to a third analog input (AIN2) terminal 416 of the analog multiplexer. A discrete calibration capacitor 420 has a first terminal connected to the circuit ground and has a second terminal connected as a fourth analog input signal to a fourth analog input (AIN3) terminal 422 of the analog multiplexer.

In the illustrated embodiment, the calibration capacitor has a capacitance of approximately 1 nanofarad.

In the illustrated embodiment, the analog multiplexer 410 has an analog output 430. The analog multiplexer is responsive to a first select signal on a first select input terminal (SEL0) 432 and a second select signal on a second select input terminal (SEL1) 434 to selectively connect one of the four analog input signals on one of the four analog inputs 410, 412, 414, 422 to the analog output. For example, if both select signals are inactive (e.g., the input states of both the SEL1 and the SEL0 inputs are logic zero (0, 0), the first sensing capacitor signal line 230 is electrically connected to the analog output. If the first select signal is active and the second select signal is inactive (e.g., the states of the SEL1, SEL0 inputs are 0, 1, respectively), the second sensing capacitor signal line 260 is electrically connected to the analog output. If the first select signal is inactive and the second select signal is active (e.g., the states of the SEL1, SEL0 inputs are 1, 0, respectively), the third sensing capacitor signal line 310 is electrically connected to the analog output. If both select signals are active (e.g., the states of the SEL1, SEL0 inputs are 1, 1, respectively), the second terminal of the calibration capacitor 420 is electrically connect to the analog output.

In the illustrated embodiment, the analog multiplexer 410 is implemented as a 74HC4051 8-channel analog multiplexer/demultiplexer, which is commercially available from a number of vendors. Only four of the eight channels are used, and a third select signal (not shown in FIG. 18) is connected to a fixed logic value so that only the four active channels can be selected by the SEL0 and SEL1 signals as described above. The selected analog input is connected to the analog output with a low on-resistance of less than 100 ohms. The analog multiplexer is provided with the auxiliary voltage (AUX_VCC) and consumes power only when the auxiliary voltage is enabled as described below.

The analog output 430 of the analog multiplexer 410 is connected to an input terminal 452 to a clock generator 450. As described in more detail below, the clock generator is implemented in the illustrated embodiment as an astable multivibrator, which may also be referred to as a relaxation oscillator. The clock generator generates an output signal on an output terminal 454. The output signal is a square-wave signal having a frequency responsive to the magnitude of the capacitance between the input terminal and ground. Thus, the clock generator is responsive to the capacitance on the input currently selected by the analog multiplexer. As described in more detail below, the clock generator is configured to have a nominal frequency of approximately 488 kHz if no external capacitance were connected to the input terminal. The clock generator is responsive to the capacitance selectively coupled through the analog multiplexer to decrease the frequency of the output signal as further described below. The clock generator is provided with the auxiliary voltage (AUX_VCC) and consumes power only when the auxiliary voltage is enabled as described below.

The square-wave output signal on the output terminal 454 of the clock generator 450 is provided as an input to a digital input terminal (DIN0) 502 of a micro-control unit (MCU) 500. The MCU processes the square-wave signal to in a manner described below. In the illustrated embodiment, the MCU is implemented as an STM32L0x1 microcontroller, which is commercially available from STMicroelectronics of Geneva, Switzerland. Other microcontrollers may also be used as the MCU. In FIG. 18, only the input terminals and output terminals of the MCU used to implement the sensing and communication system 400 are shown and described. As shown in FIG. 18, the MCU is connected directly to the battery power on the VCC bus 210 and receives power continuously; however, the MCU has very low power consumption when operating and spends a large percentage of time in a hibernating mode in which the MCU consume even less power.

The MCU 500 has a first digital output terminal (DOUT0) 510 and a second digital output terminal (DOUT1) 512, which are connected to the first select terminal (SEL0) 432 and the second select terminal (SEL1) 434 of the analog multiplexer 410. The MCU controls the logic states on the two digital output terminals to cause the analog multiplexer to couple a selective one of the first analog input (AIN0) terminal 412, the second analog input (AIN1) terminal 414, the third analog input (AIN2) terminal 416 or the fourth analog input (AIN3) terminal 422 to the analog output terminal 430. For example, in one embodiment, the MCU first sets the logic states of the first digital output terminal and the second digital output terminal to 0 and 0, respectively, to cause the analog multiplexer to connect the signal line 230 from the upper capacitive sensor 220 to the analog output of the multiplexer. The multivibrator 450 generates a square-wave on the output 454 having a frequency responsive to the capacitance of the upper capacitive sensor. While the first and second digital output terminals are maintained in the 0, 0 logic states, the MCU processes the square-wave in the manner described below and generates a first value associated with the capacitance of the upper capacitive sensor. The MCU next sets the logic states of the first digital output terminal and the second digital output terminal to 0 and 1, respectively, to cause the analog multiplexer to connect the signal line 260 from the middle capacitive sensor 250 to the analog output of the multiplexer. The multivibrator generates a square-wave on the output having a frequency responsive to the capacitance of the middle capacitive sensor. While the first and second digital output terminals are maintained in the 0, 1 logic states, the MCU processes the square-wave in the manner described below and generates a second value associated with the capacitance of the middle capacitive sensor. The MCU next sets the logic states of the first digital output terminal and the second digital output terminal to 1 and 0, respectively, to cause the analog multiplexer to connect the signal line 310 from the lower capacitive sensor 300 to the analog output of the multiplexer. The multivibrator generates a square-wave on the output having a frequency responsive to the capacitance of the lower capacitive sensor. While the first and second digital output terminals are maintained in the 1, 0 logic states, the MCU processes the square-wave in the manner described below and generates a second value associated with the capacitance of the lower capacitive sensor. The MCU next sets the logic states of the first digital output terminal and the second digital output terminal to 1 and 1, respectively, to cause the analog multiplexer to connect the calibration capacitor 420 to the analog output of the multiplexer. The multivibrator generates a square-wave on the output having a frequency responsive to the capacitance of the calibration capacitor. While the first and second digital output terminals are maintained in the 1, 1 logic states, the MCU processes the square-wave in the manner described below and generates a second value associated with the capacitance of the middle capacitive sensor. In other embodiments, the MCU may change the logic states of the first and second digital output terminals in a different sequence.

The MCU 500 includes a second digital input terminal (DIN1) 520, which is connected to the output terminal 532 of a digital magnetic switch 530. In the illustrated embodiment, the magnetic switch has a power terminal 534 and a ground terminal 536. The power terminal is connected to the VCC bus 210 from the battery 200. The ground terminal is connected to the ground reference 402. The output terminal of the magnetic switch is coupled to the power terminal by a pull-up resistor 538. In the absence of a sufficient magnetic field, the output terminal is open and is pulled up to the voltage on the power terminal by the pull-up resistor. In the presence of a sufficient magnetic field, the output terminal is pulled down to a voltage close to the voltage of the ground terminal (e.g., to logic "0"). In the illustrated embodiment, the magnetic switch is located near the upper left corner of the upper body portion 110 as shown in FIG. 1, for example. When a magnet of sufficient force is placed near the upper left core of the upper body portion, the magnetic switch operates to pull the output terminal down to a logic "0" level. The MCU detects the presence of the logic "0" level on the second digital input terminal (DIN1) and initiates a setup routine described below. In the illustrated embodiment, the digital magnetic switch is implemented by an RR120 TMR digital magnetic sensor commercially available from Coto Technology of North Kingston, R.I. Other magnetic switches from other sources may be used. In certain embodiments, the upper protective cover 114 may include an indicia 540 to indicate to a user where to move the magnet to cause the magnetic switch to close.

The MCU 500 further includes an analog input terminal (AIN0) 550. The analog input terminal is electrically connected to an analog output terminal 562 of a temperature sensor 560. The temperature sensor further includes a power input terminal 564 and a ground reference terminal 566. The temperature sensor is provided with the auxiliary voltage (AUX_VCC) and consumes power only when the auxiliary voltage is enabled as described below.

In the illustrated embodiment, the temperature sensor 560 comprises an MCP9700 low-power linear active thermistor integrated circuit, which is commercially available from Microchip Technology of Chandler, Ariz. The temperature sensor includes internal active circuitry that converts a sensed ambient temperature into the magnitude of an output voltage on the analog output terminal. For example, the output voltage of the illustrated temperature sensor changes substantially linearly from approximately 250 millivolts at approximately −25° C. to approximately 1,250 millivolts at approximately +125° C. Basically, the output voltage increases by approximately 10 millivolts for each 1° C. increase in temperature. Temperature sensors from other suppliers having different output voltage characteristics in response to temperature may also be used with suitable modifications. The MCU monitors the analog voltage VIN on the analog input terminal and converts the analog voltage temperature according to the following equation:

$$T(°C.) = \frac{V_{IN} - 500 \text{ mV}}{10 \text{ mV}/°C.}$$

For example, an input voltage of 750 millivolts corresponds to an ambient temperature of approximately 25° C., and an input voltage of approximately 1,000 millivolts corresponds to an ambient temperature of approximately 50° C.

In the illustrated embodiment, the temperature sensor 560 is located on the upper body portion 110 just above the first transition location 126 separating the upper body portion from the lower body portion 112 such that the temperature sensor is buried approximately 35-40 millimeters below the surface level of the soil when the uppermost end 124 of the upper body portion is substantially even with the surface level of the soil.

The MCU 500 communicates with a radio transceiver 570 having an antenna terminal (ANT) 572, which is coupled to a chip antenna 574 via an impedance matching circuit (Z) 576. In the illustrated embodiment the radio transceiver comprises a module based on the Semtech RF transceiver chip SX1276. The module comprises a LoRa1276-C1 100-milliwatts long range spread spectrum wireless transceiver module, which is commercially available from NiceRF Wireless Technology Co., Ltd., of Shenzhen, China. Similar RF transceiver modules from other sources may also be used.

In one embodiment, the antenna 572 comprises an ANT1204LL05R0915AFR4 chip antenna, which is commercially available from Yageo Corporation of Taipei, Taiwan. Other antennas from other sources may also be used. The antenna is positioned in a second front ungrounded area 578, which is juxtaposed with the first rear ungrounded area 186.

In the illustrated embodiment, the impedance matching circuit 576 comprises a conventional pi-pad attenuator having a series resistor between two shunt resistors to ground. The pi-pad attenuator may include an optional series input resistor from the antenna.

The MCU 500 receives data from the radio transceiver 570 via a conventional MISO (Master In, Slave Out) Serial Peripheral Interface (SPI) signal on a terminal 580, which is connected to a corresponding MISO terminal 582 of the radio transceiver. The MCU sends data to the radio transceiver via an MOSI (Master Output, Slave Input) terminal 584, which is connected to a corresponding MOSI terminal 586 of the radio transceiver. An SCK (serial clock for SPI interface) terminal 590 of the MCU is connected to a corresponding SCK terminal 592 of the radio transceiver. An NSS (SPI enable) terminal 594 of the MCU is connected to a corresponding NSS terminal 596 of the radio transceiver. The MCU activates the NSS terminal to enable the radio transceiver to receive and send data. The MCU and the radio transceiver use conventional SPI protocols to communicate commands and data from the MCU to the radio transceiver and to communicate data and status information from the radio transceiver to the MCU to implement the communications described below.

A RESET output terminal 600 of the MCU 500 is connected to an NRESET input terminal 602 of the radio transceiver 570. The MCU selectively activates the RESET output terminal to a low (e.g., ground) logic level to reset the radio transceiver to a known initial state.

The radio transceiver 570 further communicates with the MCU 500 via a first digital output signal generated on a first digital output (DIO0) terminal 610. The first digital output terminal is coupled to a first digital input (PA3) terminal 612 of the MCU. The radio transceiver also communicates with the MCU via a second digital output signal generated on a second digital output (DIO1) terminal 614. The second digital output is coupled to a second digital input (PA2) terminal 612 of the MCU. In the illustrated embodiment, the radio transceiver generates signals on the two digital output terminals as interrupts to the MCU to signal the status of the radio transceiver to the MCU.

The MCU 500 also includes a reset (NRST) input terminal 652 that is connected to a first terminal 654 of a test connector 650. The MCU includes a test data (SWDIO) input/output terminal 656 that is connected to a second terminal 658 of the test connector. The MCU includes a test clock (SWDCLK) input terminal 660 that is connected to a third terminal 662 of the test connector. A fourth terminal 664 of the test connector is connected to the voltage bus (VCC) 210, and at least a fifth terminal 666 is connected to the ground reference 402. In the illustrated embodiment, the test connector comprises a plurality of circuit board pads configured to be compatible with a 10-pin Tag-Connect cable, which is commercially available from Tag-Connect, LLC, of Burlingame, Calif. Other test connector systems may also be used. The test connector is accessible prior to installation of the protective cover 114 and may be used to test the functionality of the sensing and communication system 400 prior to delivery.

Figure 19:
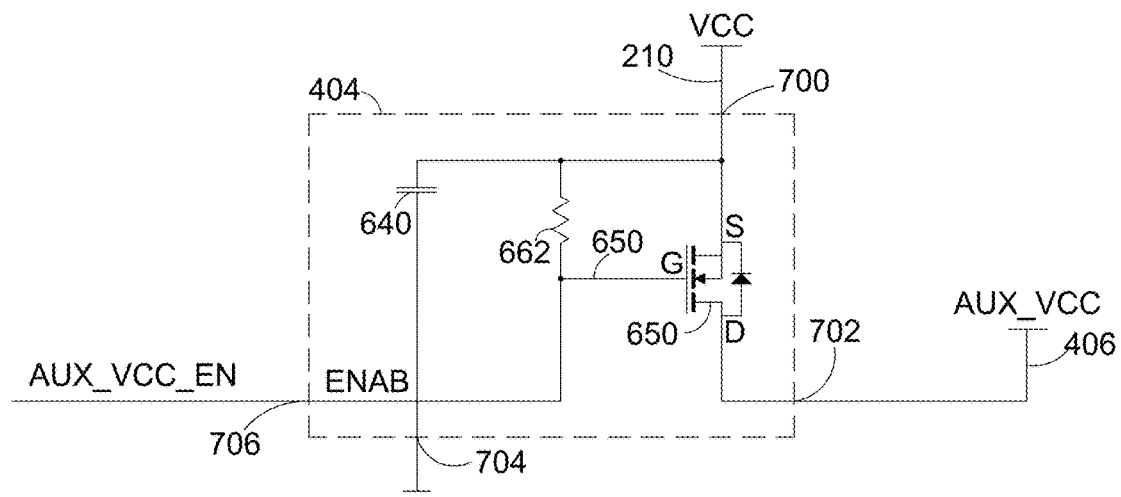
FIG. 19 illustrates a more detailed schematic diagram of the auxiliary power control circuit of FIG. 17.

The auxiliary voltage switch 404 is shown in more detail in FIG. 19. In the illustrated embodiment, the auxiliary voltage switch receives the battery voltage (VCC) on a voltage input (VIN) terminal 700 and provides the auxiliary output voltage (AUX_VCC) on a voltage output (VOUT) terminal 702. A ground terminal 704 is connected to the circuit ground 402. The auxiliary voltage switch is controlled by an auxiliary voltage switch enable (AUX_VCC_EN) signal, which is received on an enable (ENAB) input terminal 706. As illustrated in FIG. 18, the auxiliary voltage switch enable signal is provides as an output from the MCU 500 on a switch enable (SWENAB) output terminal 710.

The auxiliary voltage switch 404 includes a power metal oxide semiconductor field effect transistor (MOSFET) 720 having a source (S) terminal, a drain (D) terminal and a gate (G) terminal. In the illustrated embodiment, the power MOSFET comprises a P-channel enhancement mode MOSFET having a low on-resistance (e.g., less than 1 ohm) from the source terminal to the drain terminal when the voltage on the gate terminal is sufficiently negative with respect to the source terminal. In the illustrated embodiment, the power MOSFET may be an Si2309CDS MOSFET commercially available from Vishay Intertechnology, Inc., of Malvern, Pa., or a similar device from other sources.

In the illustrated embodiment, the voltage provided by the battery 200 is approximately 3 volts; and the power MOSFET 720 turns on when the MCU 500 causes the voltage on the switch enable signal applied to the enable input terminal 706 to be at or near 0 volts. When the power MOSFET is turned on, a low resistance conductive path is provided from the battery voltage (VCC) in voltage input terminal 700 to the voltage output terminal 702 of the auxiliary voltage switch 404 such that the auxiliary voltage on the voltage output terminal has a magnitude close to the magnitude of the battery voltage less a voltage drop from the source terminal to the drain terminal of the power MOSFET. In view of the low on-resistance and the low current requirements for the circuits supplied with the auxiliary voltage, the magnitude of the auxiliary voltage is almost 3 volts.

As shown in FIG. 18, the auxiliary voltage (AUX_VCC) from the auxiliary voltage switch 404 is provided to the analog multiplexer 410, to the clock generator 450, to temperature sensor 560, and to the radio transceiver 570. Accordingly, the four components are only powered on when the auxiliary voltage is being generated.

Figure 20:
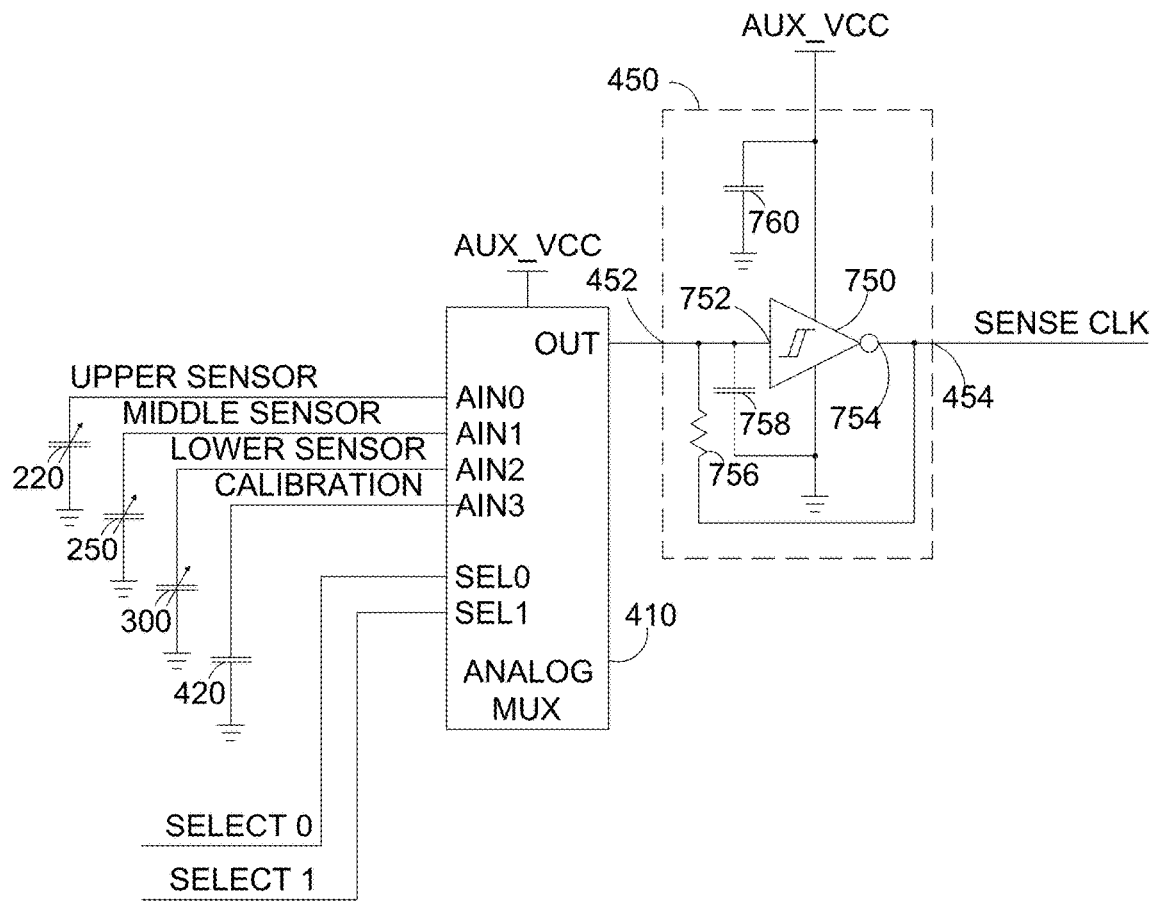
FIG. 20 illustrates a more detailed schematic diagram of the analog multiplexer and the oscillator circuit of FIG. 17.

The clock generator 450 is shown in more detail in FIG. 20. The analog multiplexer 410 is shown to assist in understanding the variable frequency operation of the clock generator. The input terminal 452 of the clock generator is connected to an input 752 of an inverter 750. In the illustrated embodiment, the inverter comprises a Schmitt-trigger inverter such as, for example, an SN74AHC1G14 single inverter gate, which is commercially available from Texas Instruments of Dallas, Tex. An equivalent circuit from other sources may also be used. The inverter has an output 754 that is connected back to the input of the inverter by a timing resistor 756. A base timing capacitor 758 is connected from the input of the inverter to the circuit ground reference. Thus, the base timing capacitor is connected in parallel with the capacitance on the input currently selected by the analog multiplexer 410. The base timing capacitor establishes a maximum operating frequency of the clock generator. In the illustrated embodiment, the base timing capacitor has a capacitance of approximately 250 nanofarads, and the timing resistor has a resistance of approximately 10,000 ohms to provide a nominal base frequency of approximately 488 kHz. The effect of selectively connecting one of the sensing capacitances or the calibration capacitor in parallel with the base timing capacitor has the effect of lowering the frequency as will be discussed in more detail below. For example, selecting the calibration capacitor 420 lowers the frequency to about 486 kHz. Selecting the upper sensing capacitor 220 lowers the frequency to about 470 kHz in dry soil and lowers the frequency to approximately 360 kHz in very wet soil. Selecting the middle sensing capacitor 250 lowers the frequency to about 420 kHz in dry soil and lowers the frequency to approximately 180 kHz in very wet soil. Selecting the bottom sensing capacitor 300 lowers the frequency to about 430 kHz in dry soil and lowers the frequency to approximately 200 kHz in very wet soil. The actual frequency values may vary from unit to unit and can be determined in a calibration procedure performed prior to deployment of each unit. In the illustrated embodiment, a filter capacitor 760 is positioned close to the auxiliary power input of the inverter.

A plurality of the moisture sensing units 100 are deployed in a landscaped area 770 having a plurality of watering devices (not shown) controlled by master controller 780. Each of the moisture sensing units is in bidirectional communication with the master controller via the respective radio transceiver 570 (FIG. 18) within each moisture sensing unit and a corresponding radio transceiver (not shown) within the master controller. In the illustrated embodiment, the moisture sensing units may be spaced apart from the master controller by a distance up to at least 150 meters (approximately 490 feet). The master controller receives data from each moisture sensing unit within a respective watering area and determines the current moisture conditions proximate to each moisture sensing unit. The master controller determines the quantity of water that needs to be applied in each watering area based on the current moisture conditions in the watering area and based on other information (e.g., forecasted precipitation, forecasted wind conditions, current and forecasted air temperatures, and the like). For example, the master controller may also communicate with a weather service 790 via an Internet connection 792 to the Cloud 794. The master controller may also communicate with a user interface on a smartphone 796 (or other computer system (not shown)) via a Wi-Fi connection 798 or via the Internet connection and the Cloud.

Figure 22:
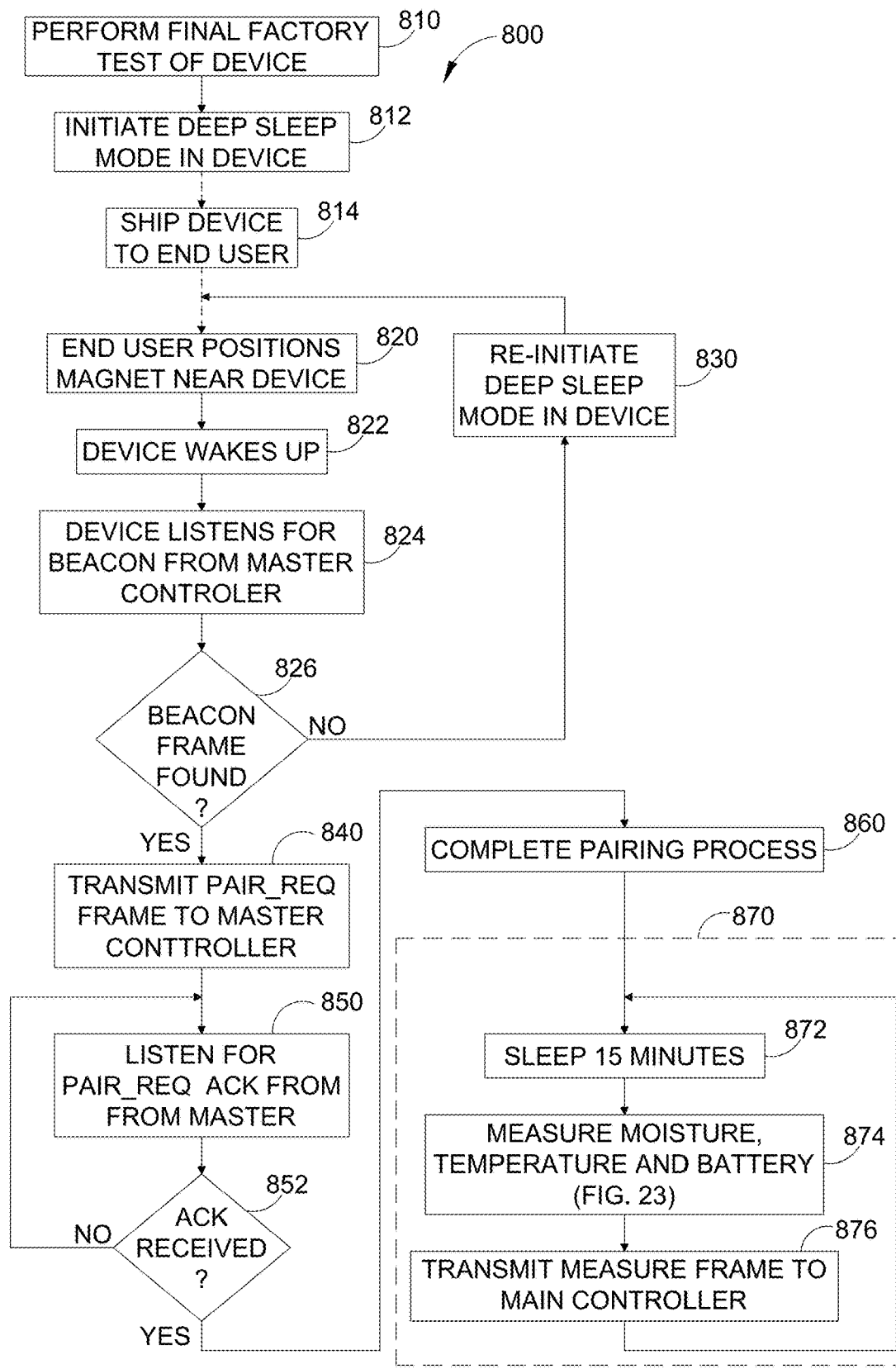
FIG. 22 illustrates a flowchart of the initial commissioning, shipping, initiation and deployment of the moisture sensing unit of FIGS. 1-20.

The overall operation of the sensing and communication system 400 is illustrated by a flowchart 800 in FIG. 22. In a first step 810 following the manufacturing of the moisture sensing unit 100, the unit is tested in the factory to verify proper operation. After the final factory test, the moisture sensing unit is placed in a deep sleep mode in a step 812. As discussed above, in the deep sleep mode, the auxiliary voltage switch 404 is disabled such that the components connected to the auxiliary voltage are unpowered. Furthermore, the MCU 500 is placed into a low-power sleep mode. The moisture sensing unit consumes very little power and the battery 200 is able to supply the power consumed by the MCU for approximately fourteen years. In a step 814, the moisture sensing unit is shipped to an end-user. The shipping may be direct or through intermediaries.

Figure 21:
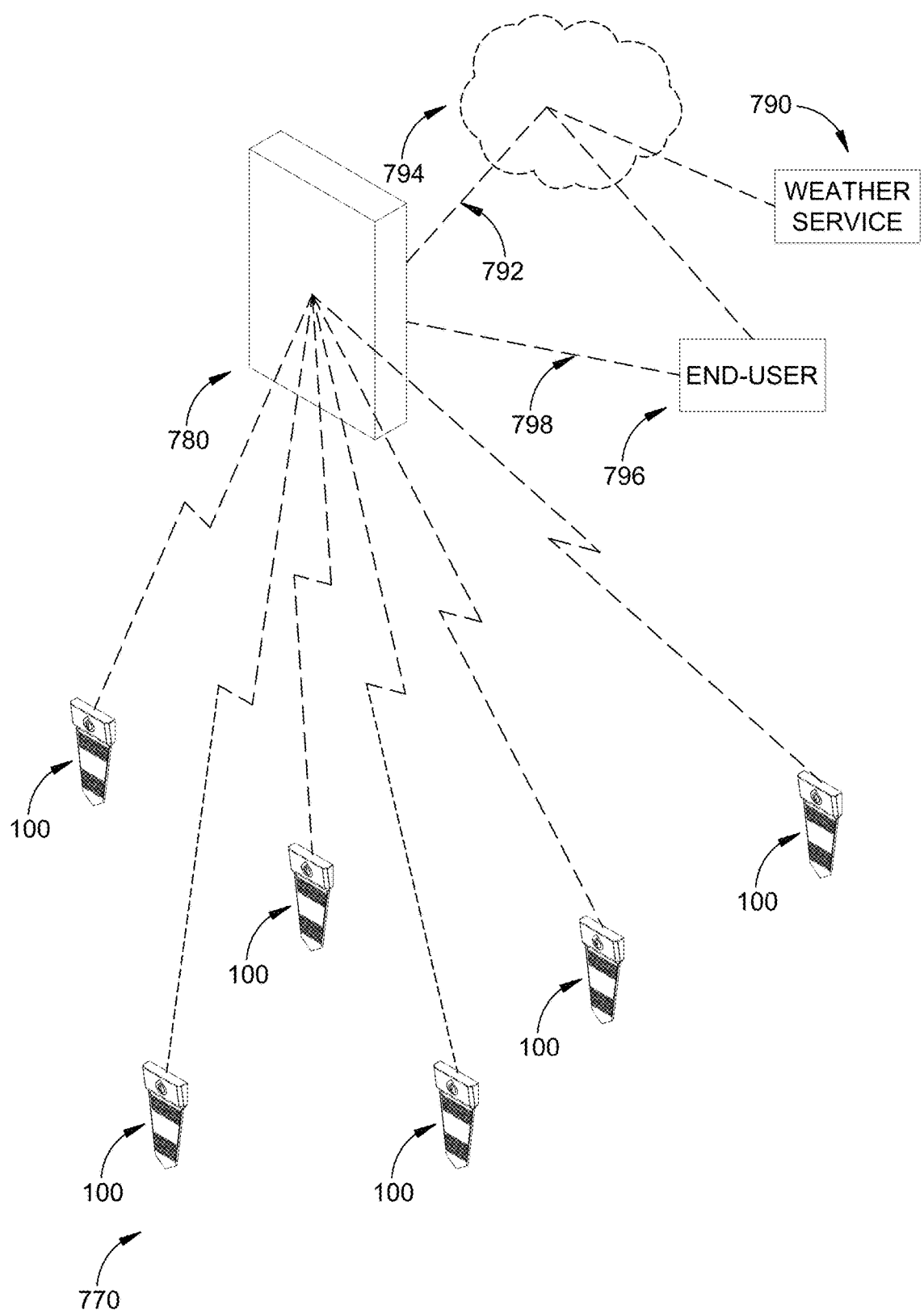
FIG. 21 illustrates a pictorial block diagram of an irrigation control system in which a plurality of deployed wireless moisture sensors are communicating with an irrigation controller.

After the moisture sensing unit 100 is obtained by an end user and the end user is ready to deploy the unit, the end user moves a magnet near the indicia 540 on the upper protective cover 114 in a step 820 to activate the magnetic switch 530 (FIG. 18). The signal applied to the MCU 500 causes the MCU to wake from the low-power sleep mode in a step 822. In a step 824, the MCU sends commands to the radio transceiver 570 to cause the radio transceiver to start listening for a beacon from a master controller 780 (FIG. 21) to which the moisture sensing unit is to be paired. If the MCU determines that a beacon has not been received in a decision step 826, the MCU proceeds to a step 830 wherein the MCU turns off the auxiliary voltage and then re-enters the low-power sleep mode. Accordingly, this step prevents the MCU from staying awake if the moisture sensing unit is inadvertently positioned close to a magnet or other magnetic source during shipping or at any other time prior to an intended deployment of the moisture sensing unit.

If the MCU 500 determines that a beacon has been found in the decision step 826, the MCU proceeds to a step 850 wherein the MCU sends data and commands to the radio transceiver 570 to cause the radio transceiver to send a pair request (PAIR_REQ) frame to the master controller. The MCU then listens for a pair request acknowledgement (PAIR_REQ_ACK) from the master controller in a step 852. If a pair request acknowledgement is not received, the MCU branches from a decision step 854 back to the step 852 and continues to listen for the pair request acknowledgement. When the pair request acknowledgement is received, the MCU braches from the decision step 854 to a step 860 wherein the MCU communicates with the master controller via the radio transceiver to complete the pairing process in a conventional manner. After completing the pairing process, the MCU enters a recurring measurement and transmission loop 870 wherein the MCU controls the analog multiplexer 410 to perform the capacitance measurements and transmits the measurements to the master controller.

Within the measurement and transmission loop 870, the MCU 500 sleeps for 15 minutes (e.g., turns off the auxiliary voltage and enters the deep sleep, low-power mode) in a step 872. An internal timer within the MCU wakes the MCU after 15 minutes, and the MCU performs a step 874 wherein the MCU measures the moisture content (e.g., determines the capacitance of each of the three capacitive sensors (220, 250, 300). The MCU also measures the temperature via the temperature sensor 560. The MCU also determines the current magnitude of the voltage from the battery 200 by internally comparing the VCC supply voltage to an internal voltage reference. The step 874 is illustrated in more detail in FIGS. 23 and 24. After completing the measurements, the MCU performs a step 876 wherein MCU sends commands and data to the radio transceiver 570 to cause the radio transceiver to transmit the measurements to the master controller 780. The radio transceiver uses collision detection and encoding protocols to interleave the transmissions with transmissions from other moisture sensing units 100 communicating with the same master controller. The framing and transmission of the data in a multiple unit environment is well known to the art and is not disclosed herein. In the illustrated embodiment, the data is transmitted from one of the moisture sending units to the master controller in the following 16-byte format:

| | |
|---|---|
| Header/message_type | 1 byte |
| Header/sequence | 1 byte |
| Header/source_address | 2 bytes |
| Payload/calibration_value | 2 bytes |
| Payload/top_value | 2 bytes |
| Payload/middle_value | 2 bytes |
| Payload/bottom_value | 2 bytes |
| Payload/temperature | 2 bytes |
| Payload/battery_voltage | 2 bytes |

The radio transceiver 570 adds further framing and cyclic redundancy checking (CRC) data to the data being transmitted in a conventional manner.

Figure 25:
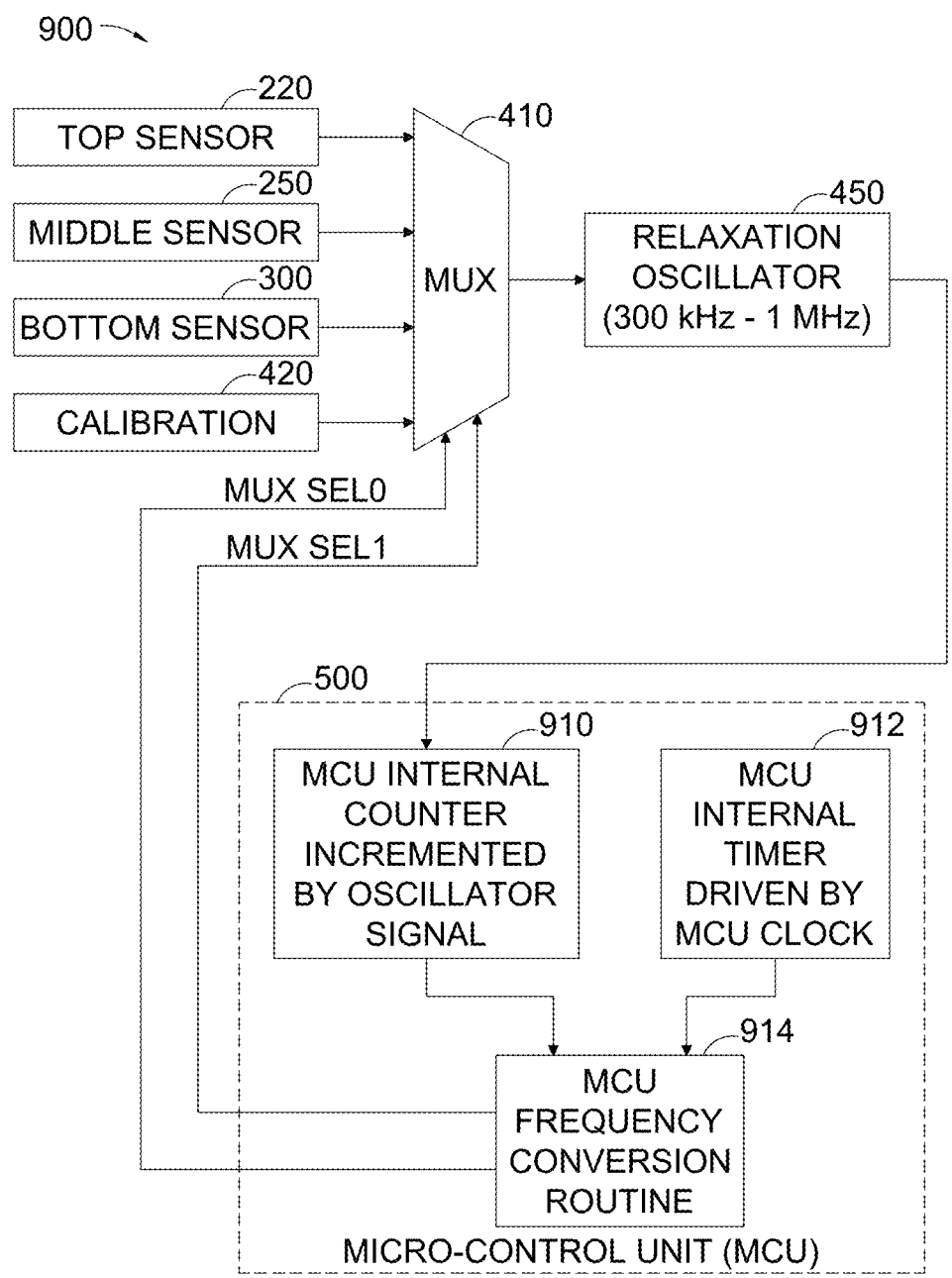
FIG. 25 illustrates a functional block diagram of the operation of the components of the capacitance measurements performed by the moisture sensing unit of FIGS. 1-20.

The operation of the step 874 of FIG. 23 can also be understood in view of a simplified functional block diagram 900 in FIG. 25. In FIG. 25, the sensors 220, 250, 300, the calibration capacitor 420, the analog multiplexer 410, the clock generator (relaxation oscillator) 450 and the MCU 500 are connected as shown in FIG. 18. The MCU includes internal hardware and software that implements an internal counter 910, which is incremented by the signal from the clock generator. The MCU first activates the multiplexer selection signals (MUX SEL 0 and MUX SEL 1) to the multiplexer to select one of the four inputs to the multiplexer. The MCU resets the internal counter to a known value (e.g., zero) and then enables the internal counter to start counting. At substantially the same time, the MCU starts an internal timer 912 that either counts up from zero to a known value or counts down from a known value to zero. For example, the internal timer may be set to count up or down for 1 millisecond. When the internal timer times out, the count is complete, and the MCU inputs reads and stores the current count on the counter value. The MCU converts the count value to a frequency value. In the illustrated example, the number of counts received in 1 millisecond are multiplied by 1,000 to calculate the frequency from the clock generator in kHz. The MCU then activates the multiplexer selection signals with a different combination of values to select a different input to the multiplexer and controls the counter and the timer in a similar manner to obtain a count (e.g., frequency) value for the next input. The actions are repeated for each of the four inputs during each of the wake cycles.

After obtaining the count (frequency) information for each sensor and the calibration capacitor, the MCU 500 sends the information to the irrigation controller 780 (FIG. 21) for processing. In addition to the measured count information, the MCU sends the measured temperature and the measured voltage to the irrigation controller. Within the irrigation controller (or within the cloud 794), the measured counts (frequencies) for the three sensors are compared to the measured count (frequency) for the calibration capacitor to normalize the frequencies. The normalized frequencies are then used to calculate the current capacitances of the three sensors relative to the capacitance of the calibration capacitor. The calculated capacitances are compared with a set of corresponding capacitances determined in a controlled environment to determine the percentage increase in each sensor capacitance. The percentage increases are used to determine the approximate moisture content at each of the three depths of the moisture sensing unit 100. The calibration information for each moisture sensing unit may be maintained in the irrigation controller; however, in the illustrated embodiment, the calibration information for each moisture sensing unit is stored in the cloud prior to shipment of the moisture sensing unit. In certain embodiments, the calculations that convert the raw frequency data to moisture data are performed within an application stored in the cloud.

The foregoing processing and transmission steps occur in approximately 100 milliseconds during which the auxiliary voltage is turned on. The auxiliary voltage is turned off and the MCU 500 enters the lower power sleep for the remaining portion of each 15-minute cycle. Thus, the increased power consumption has a duty cycle of approximately 0.00011 (e.g., 0.01%), which results in a potential battery life of approximately seven years. The duty cycle can be modified by commands received by the moisture sensing unit 100 from the master controller 780. For example, the moisture sensing unit can be configured to wake every 30 minutes to reduce power consumption. In colder climates where irrigation is halted during certain months, the moisture sensing unit can be commanded to remain asleep for longer durations to further reduce power consumption.

As various changes could be made in the above constructions without departing from the scope of the invention, it is intended that all the matter included in the above description or shown in the accompanying drawings shall be interpreted as illustrative and not in a limiting sense.

What is claimed is:

1. A moisture sensor insertable into soil, the moisture sensor comprising:
    a printed circuit board having an upper end and a lower end and having a front surface and a rear surface;
    a first capacitive sensor positioned on one of the front surface and the back surface of the printed circuit board and positioned in a first selected location with respect to the upper end of the printed circuit board, the first capacitive sensor having a first capacitance responsive to moisture content of soil proximate to the first capacitive sensor;
    a second capacitive sensor positioned on one of the front surface and the back surface of the printed circuit board and positioned in a second selected location with respect to the upper end of the printed circuit board, the second selected location farther from the upper end than the first selected location, the second capacitive sensor having a second capacitance responsive to moisture content of soil proximate to the second capacitive sensor;
    a third capacitive sensor positioned on one of the front surface and the back surface of the printed circuit board and positioned in a third selected location with respect to the upper end of the printed circuit board, the third selected location farther from the upper end than the second selected location, the third capacitive sensor having a third capacitance responsive to moisture content of soil proximate to the third capacitive sensor; and
    a processing and transmission subsystem positioned on at least one of the front surface and the back surface of the printed circuit board proximate to the upper end of the printed circuit board, the processing and transmission subsystem coupled to each of the first, second and third capacitive sensors, the processing and transmission subsystem generating a first data value responsive to the first capacitance, generating a second data value responsive to the second capacitance and generating a third data value responsive to the third capacitance, the processing and transmission subsystem transmitting the first, second and third data values via a radio frequency output signal.

2. The moisture sensor as defined in claim 1, wherein the processing and transmission subsystem includes a capacitor having a fixed fourth capacitance substantially unaffected by the moisture content of the soil proximate to the moisture sensor, the processing and transmission subsystem generating a calibration data value responsive to fourth fixed fourth capacitance and transmitting the calibration data value along with the first, second and third data values.

3. The moisture sensor as defined in claim 1, wherein the processing and transmission subsystem includes a temperature sensor that generates an electrical output signal responsive to the temperature of soil proximate to the temperature sensor, the processing and transmission subsystem generating a temperature sensor data value and transmitting the temperature sensor data value along with the first, second and third data values.

4. The moisture sensor as defined in claim 1, wherein the processing and transmission subsystem includes:
    an analog multiplexer having at least a first analog input connected to the first capacitive sensor, a second analog input connected to the second capacitive sensor and a third analog input connected to the third capacitive sensor, the analog multiplexer having an analog output, the analog multiplexer controlled to selectively connect the first capacitive sensor to the analog output for a first time duration, to selectively connect the second capacitive sensor to the analog output for a second time duration and to selectively connect the third capacitive sensor to the analog output for a third time duration;
    a capacitance-controlled oscillator having an input coupled to the analog output of the capacitor and having an output that generates clock signal, the oscillator responsive to the first capacitive sensor connected to the analog output to generate the clock signal at a first frequency during the first time duration, the oscillator responsive to the second capacitive sensor connected to the analog output to generate the clock signal at a second frequency during the second time duration, the oscillator responsive to the third capacitive sensor connected to the analog output to generate the clock signal at a third frequency during the third time duration; and
    a processor that receives the clock signal from the oscillator, the processor determining the first frequency to generate the first data value, determining the second frequency to generate the second data value and determining the third frequency to generate the third data value.

5. The moisture sensor as defined in claim 4, wherein:
    the processing and transmission subsystem includes a calibration capacitor having a fixed fourth capacitance substantially unaffected by the moisture content of the soil proximate to the moisture sensor;
    the analog multiplexer is controlled to selectively connect the calibration capacitor to the analog output for a fourth time duration;
    the oscillator is responsive to the calibration capacitor connected to the analog output to generate the clock signal at a fourth frequency during the fourth time duration; and
    the processor determines the fourth frequency to generate a calibration data value, the processing and transmission subsystem transmitting the calibration data value in the radio frequency output signal along with the first, second and third data values.

6. A method for determining moisture content of soil at three spaced apart levels below the surface of the soil, the method comprising:
- inserting a moisture sensing unit into the soil with a first capacitive sensor at a first level below the soil surface, with a second capacitive sensor at a second level below the soil surface, the second level farther below the soil surface than the first level, and with a third capacitive sensor at a third level below the soil surface, the third level farther below the soil surface than the second level;
- selecting the first capacitive sensor as an input to a capacitively controlled clock generator during a first time duration, the clock generator generating an output clock signal at a first frequency, the first frequency responsive to a capacitance of the first capacitive sensor, the capacitance of the first capacitive sensor responsive to the moisture content of soil proximate to the first capacitive sensor at the first level;
- selecting the second capacitive sensor as an input to the clock generator during a second time duration, the clock generator generating the output clock signal at a second frequency, the second frequency responsive to a capacitance of the second capacitive sensor, the capacitance of the second capacitive sensor responsive to the moisture content of soil proximate to the second capacitive sensor at the second level;
- selecting the third capacitive sensor as an input to the clock generator during a third time duration, the clock generator generating the output clock signal at a third frequency, the third frequency responsive to a capacitance of the third capacitive sensor, the capacitance of the third capacitive sensor responsive to the moisture content of soil proximate to the third capacitive sensor at the third level;
- determining the first frequency and generating a first data value responsive to the first frequency;
- determining the second frequency and generating a second data value responsive to the first frequency;
- determining the third frequency and generating a third data value responsive to the third frequency; and
- transmitting the first, second and third data values via a radio frequency signal as representations of the moisture content of the soil at the first, second and third levels, respectively.

7. The method as defined in claim 6, further including:
- selecting a calibration capacitor as an input to the clock generation during a fourth time duration, the clock generator generating the output clock signal at a fourth frequency, the fourth frequency responsive to a capacitance of the calibration capacitor;
- determining the fourth frequency and generating a calibration data value responsive to the fourth frequency; and
- transmitting the calibration data value along with the first, second and third data values via the radio frequency signal.

8. The method as defined in claim 6, further comprising:
- generating an electrical output signal responsive to the temperature of soil proximate to the temperature sensor;
- generating a temperature sensor data value responsive to the electrical output signal; and
- transmitting the temperature sensor data value along with the first, second and third data values via the radio frequency signal.

9. The method as defined in claim 6, wherein:
- the first capacitive sensor, the second capacitive sensor and the third capacitive sensor are selected via an analog multiplexer that couples a selected one of the capacitive sensors to an analog output of the analog multiplexer: and
- the analog output of the analog multiplexer is coupled to an input of the clock generator, the clock generator generating the clock signal at a frequency responsive to the capacitance of the respective capacitive sensor selected by the analog multiplexer; and
- the frequency of the clock signal from the clock generator is determined for each selected capacitive sensor to produce a respective data value responsive to the frequency for each selected capacitive sensor and thereby responsive to the respective capacitance of each selected capacitive sensor, the capacitance increasing with increased moisture content, the frequency decreasing with increased moisture content.

10. The moisture sensor as defined in claim 9, wherein:
- the analog multiplexer selects a calibration capacitor during a fourth time duration, the calibration capacitor having a fixed capacitance substantially unaffected by the moisture content of the soil proximate to the moisture sensor;
- the clock generator is responsive to the calibration capacitor connected to the analog output to generate the clock signal at a fourth frequency during the fourth time duration; and
- the fourth frequency of the clock signal is determined to produce a fourth data value responsive to the fourth frequency and thereby responsive to the capacitance of the calibration capacitor, the fourth data value transmitted with the first, second and third data values to provide a reference value for comparison with the first, second and third data values.

* * * * *